US009975983B2

(12) United States Patent
Lu et al.

(10) Patent No.: US 9,975,983 B2
(45) Date of Patent: May 22, 2018

(54) BIO-REDUCIBLE SELF-ASSEMBLED LIQUID CRYSTALLINE BLOCK COPOLYMER FOR DRUG DELIVERY

(71) Applicant: UNIVERSITY OF CONNECTICUT, Farmington, CT (US)

(72) Inventors: Xiuling Lu, Storrs, CT (US); Rajeswari Kasi, Bala Cynwyd, PA (US); Thanh-Huyen Tran, Willington, CT (US); Chi Thanh Nguyen, Willington, CT (US)

(73) Assignee: University of Connecticut, Farmington, CT (US)

( * ) Notice: Subject to any disclaimer, the term of this patent is extended or adjusted under 35 U.S.C. 154(b) by 0 days. days.

(21) Appl. No.: 15/519,085

(22) PCT Filed: Oct. 15, 2015

(86) PCT No.: PCT/US2015/055660
§ 371 (c)(1),
(2) Date: Apr. 13, 2017

(87) PCT Pub. No.: WO2016/061310
PCT Pub. Date: Apr. 21, 2016

(65) Prior Publication Data
US 2017/0240680 A1 Aug. 24, 2017

Related U.S. Application Data

(60) Provisional application No. 62/064,041, filed on Oct. 15, 2014.

(51) Int. Cl.
*A61K 9/51* (2006.01)
*C08F 293/00* (2006.01)
*A61K 31/704* (2006.01)

(52) U.S. Cl.
CPC ........ *C08F 293/005* (2013.01); *A61K 9/5138* (2013.01); *A61K 9/5192* (2013.01); *A61K 31/704* (2013.01)

(58) Field of Classification Search
None
See application file for complete search history.

(56) References Cited

U.S. PATENT DOCUMENTS

2013/0096288 A1 4/2013 Han et al.

OTHER PUBLICATIONS

Zhou et al. (Synthesis and characterization of Polycholesteryl methacrylate-polyhydroxyethyl methacrylate block copolymers; Journal of Polymer Science Part A: Polymer Chemistry 2008, vol. 46, Issue 20, pp. 6801-6809).*
International Search Report and Written Opinion for PCT/US2015/055660, dated Jan. 28, 2016.

(Continued)

*Primary Examiner* — Robert A Wax
*Assistant Examiner* — Melissa S Mercier
(74) *Attorney, Agent, or Firm* — McDonnell Boehnen Hulbert & Berghoff LLP

(57) ABSTRACT

The disclosure provides biodegradable amphiphilic liquid crystalline copolymers that can readily self-assemble to nanoparticles in aqueous solutions and also allow for encapsulation of hydrophobic pharmaceutically active molecules.

20 Claims, 13 Drawing Sheets

(56) References Cited

OTHER PUBLICATIONS

Chen X, Conti PS, Moats RA.In vivo near-infrared fluorescence imaging of intergrin avβ3 in brain tumor xenografts. Cancer Res 2004;64: 8009-14.
Cheng R, Feng F, Meng F, Deng C, Feijen J, Zhong Z. Glutathione-responsive nano-vehicles as a promising platform for targeted intracellular drug and gene delivery. J Control Release 2011; 152: 2-12.
Ebrahim Attia AB, Yang C, Tan JP, Gao S, Williams DF, Hedrick JL, et al. The effect of kinetic stability on biodistribution and anti-tumor efficacy of drug-loaded biodegradable polymeric micelles. Biomaterials 2013;34:3132-40.
Heino S, Lusa S, Somerharju P. Dissecting the role of the Golgi complex and lipid rafts in biosynthetic transport of cholesterol to the cell surface. Proc Natl Acad Sci USA 2000;97:8375-80.
Kim JH, Kim YS, Park K, Lee S, Nam HY, Min KH, et al. Antitumor efficacy of cisplatin-loaded glycol chitosan nanoparticles in tumor-bearing mice. J Control Release 2008;127:41-49.
Kim SH, Jeong JH, Lee SH, Kim SW, Park TG. PEG conjugated VEGF siRNA for anti-angiogenic gene therapy. J Control Release 2006;116(2):123-9.
Kwon GS and Forrest ML. Amphiphilic block copolymer micelles for nanoscale drug delivery. Drug Dev Res 2006; 67:15-22.
Lee H, Mok H, Lee S, Oh YK, Park TG. Target-specific intracellular delivery of siRNA using degradable hyaluronic acid nanogels. J Control Release 2007;119(2):245-52.
Lee, A.L.; Venkataraman, S.; Gao, S.; Hedrick, J. L.; Yang, Y.Y. The use of cholesterol-containing biodegradable block copolymers to exploit hydrophobic interactions for the delivery of anticancer drugs. Biomaterials, 2012, 33(6):1921-8.
Lin C, Zhong ZY, Lok MC, Jiang XL, Hennink WE, Feijen J, et al. Novel bioreducible poly(amido amine)s for highly efficient gene delivery. Bioconjugate Chem 2007;18(1)138-45.
Matsumoto S, Christie RJ, Nishiyama N, Miyata K, Ishii A, Oba M, et al. Environment-responsive block copolymer micelles with a disulfide cross-linked core for enhanced siRNA delivery. Biomacromolecules 2009;10(1)119-27.
Meng FH, Hennink WE, Zhong ZY. Reduction sensitive polymers and bioconjugates for biomedical applications. Biomaterials 2009;30:2180-98.
Meng FH, Zhong ZY, Feijen J. Stimuli-responsive polymersomes for programmed drug delivery. Biomacromolecules 2009;10(2):197-209.
Nagahama K, Ueda Y, Ouchi T, Ohya Y. Exhibition of Soft and Tenacious Characteristics Based on Liquid Crystal Formation by Introduction of Cholesterol Groups on Biodegradable Lactide Copolymer. Biomacromolecules 2007;8:3938-43.
Nguyen, T. H. Tran, X. Lu, R. M. Kasi, Self-assembled nanoparticles from thiol functionalized liquid crystalline brush block copolymers for dual encapsulation of doxorubicin and gold nanoparticles Polymer Chemistry 2014,5 (8), 2774-2783.
Nguyen, Chi Thanh et al. Redox-sensitive nanoparticles from amphiphilic cholesterol-based block copolymers for enhanced tumor intracellular release of doxorubicin. Nanomedicine: Nanotechnology, Biology and Medicine. 2015 (E-pub. Jul. 11, 2015), vol. 11, Issue 8. pp. 2071-2082.
Park J, Fong PM, Lu J, Russell KS, Booth CJ, Saltzman WM, et al. PEGylated PLGA nanoparticles for the improved delivery of doxorubicin. Nanomedicine 2009;5:410-18.
Peer D, Karp JM, Hong S, Farokhzad OC, Margalit R, Langer R. Nanocarriers as an emerging platform for cancer therapy. Nat Nanotechnol 2007;2: 751-60.
Ranucci. Elisabetta et al. "Poly (amidoamine) conjugates with disulfide- linked cholesterol pendants self-assembling into redox-sensitive nanoparticles." Biomacromolecules. 2008. vol. 9. Issue 10. pp. 2693-2704.
Rapoport N. Physical stimuli-responsive polymeric micelles for anti-cancer drug delivery. Prog Polym Sci 2007;32(8-9):962-90.
Read ES, Armes SP. Recent advances in shell cross-linked micelles. Chem Commun 2007;29:3021-35.
Rijcken CJF, Soga O, Hennink WE, van Nostrum CF. Triggered destabilisation of polymeric micelles and vesicles by changing polymers polarity: an attractive tool for drug delivery. J Control Release 2007;120(3):131-48.
Schmaljohann D. Thermo- and pH-responsive polymers in drug delivery. Adv Drug Deliv Rev 2006; 58:1655-70.
Wan T, Zou T, Cheng SX, Zhuo RX. Synthesis and Characterization of Biodegradable Cholesteryl End-Capped Polycarbonates. Biomacromolecules 2005;6:524-29.
Wang X, Li J, Wang Y, Cho KJ, Kim G, Gjyrezi A, et al. HFT-T, a targeting nanoparticles, enhances specific delivery of pactitaxel to folate receptor-positive tumors. ACS nano 2009;3: 3165-74.
Yinsong W, Lingrong L, Jian W, Zhang Q. Preparation and characterization of self-aggregated nanoparticles of cholesterol-modified O-carboxymethyl chitosan conjugates. Carbohydr Polym 2007;69:597-6.
Zhou. Yuxiang et al. "Synthesis and characterization of polycholesteryl methacrylate-polyhydroxyethyl methyacrylate block copolymers." Journal of Polymer Science Part A: Polymer Chemistry. 2008, vol. 46, Issue 20, pp. 6801-6809.
Thou, Yuxiang et al. "Polymers comprising cholesterol: synthesis, self-assembly, and applications." Materials. 2009 vol. 2. Issue 2, pp. 636-660.

* cited by examiner (b)

(c)

BIO-REDUCIBLE SELF-ASSEMBLED LIQUID CRYSTALLINE BLOCK COPOLYMER FOR DRUG DELIVERY

CROSS-REFERENCE TO RELATED APPLICATION

This application is a U.S. national phase of International Application No. PCT/US2015/055660, filed on Oct. 15, 2015, which claims priority to U.S. Provisional Application No. 62/064,041, filed Oct. 15, 2014, both of which are incorporated by reference herein in their entirety.

BACKGROUND OF THE INVENTION

Field of the Invention

The disclosure provides biodegradable amphiphilic liquid crystalline copolymers that can readily self-assemble to nanoparticles in aqueous solutions and also allow for encapsulation of hydrophobic pharmaceutically active molecules.

Description of the Related Art

Clinical use of drugs (e.g., anticancer drugs) is limited due to their hydrophobicity and non-specific toxicity. For example, the majority of clinically used anticancer drugs are low molecular compounds that diffuse rapidly though the body in both healthy and diseased tissue causing serious side effects. There is a growing need to develop safe and effective delivery systems for anticancer drugs. Self-assembled nanoparticle structures allow encapsulation of the anticancer drugs in the core while the hydrophilic shell allows for increased water solubility and stability. Nanoparticles with appropriate size and surface property may have opportunity to accumulate in tumor sites through the enhanced permeability and retention (EPR) effect, which results from abnormalities of tumor blood and lymphatic vasculature.

Various self-assembled nanoparticles have been developed for delivery of anticancer drugs. Unfortunately, most of these have not shown beneficial effects in clinical trials. The major obstacle for drug-delivery polymer systems is poor in vivo stability, low drug loading levels, reduced tumor targetability and slow drug release in tumor tissue and/or inside the tumor cells. Furthermore, many synthetic biodegradable copolymers upon erosion in vivo yield oligomers and monomers that adversely interact with the surrounding tissue.

Copolymers with cholesterol end-groups have also generated interest for various biomedical applications including serving as membranes for cell attachment and proliferation, forming the basis of polymeric scaffolds, and as materials with improved blood compatibility. But, reported amphiphilic polymer architectures that contain cholesterol are conjugates or linear copolymers with only one or a few cholesterol molecules. This results in low stability, limited drug loading capacity to 20% (w/w) with low encapsulation efficiency and fast drug release for these cholesterol-containing copolymers.

Redox-Sensitive nanocarriers containing disulfide bonds have received much attention for intracellular drug delivery due to the existence of a high glutathione (GSH) concentration in the tumor microenvironment and cancer cells. For instance, several groups have reported redox-sensitive polymer/DNA complexes, polyion complex micelles for siRNA delivery, crosslinked micelles, and degradable nanogels with good stability under the physiological conditions that, rapidly released encapsulated drugs in the intracellular reductive environment. However, limited information is available on the in vivo behavior of nanoparticles comprised of reductive-sensitive polymers and the interaction between the nanoparticles and tumor tissue.

SUMMARY OF INVENTION

Designing block copolymers with appropriate architecture and composition to increase drug loading capacity, but at the same time minimize the toxicity of the polymer carrier and its degradation products, still presents a challenge. Liquid crystalline polymers (LCPs) comprising cholesterol molecules have been applied in various fields such as bioactive materials and biotechnology, but only few researchers utilized LCPs for drug delivery systems. The present invention provides novel a biodegradable amphiphilic liquid crystalline copolymer ("copolymer" or "block copolymer"). The block copolymers of the disclosure readily formed self-assembled nanoparticles in aqueous solutions. These nanoparticles allowed for loading of hydrophobic drugs simply via self-assembly without sonication or homogenization procedure. The nanoparticles of the disclosure also showed excellent stability of the high steroid content hydrophobic core and demonstrated a high capacity for encapsulation of hydrophobic drugs. The hydrophilic surface also protected from reticuloendo-thelial system (RES) uptake and facilitated long circulation in body. The self-assembled block copolymer nanoparticles of the invention have good biocompatibility, high drug loading capacity, excellent stability, and can be easily manufactured in large scale, which make them suitable for drug delivery especially delivering anti-cancer drugs to tumors. Finally, the nanoparticles of the invention while being stable under physiological conditions rapidly release the encapsulated drug by cleavage of disulfide linkage under a cytosolic reducing environment following cellular entry, resulting in effective cytotoxicity to cancer cells (FIG. 1).

Importantly, the nanoparticles are capable of rapidly releasing the drugs inside the cells to yield significantly enhanced drug efficacy as compared to the non-reductive nanoparticles due to the cleavage of disulfide bonds when exposed to an intracellular reductive environment. Furthermore, the nanoparticles significantly increased the duration of the drug in the circulation, improved tumor accumulation and antitumor efficacy, significantly reduced toxicity compared to the free anticancer drug, and decreased cardiac accumulation of the drug. These properties make the nanoparticles of the disclosure especially suitable for use in anti-cancer drug delivery.

Finally, the copolymers of the disclosure may be functionalized (for example, with thiol, phosphate, carboxylic acid groups, etc.), and such copolymers also self-assembled in aqueous media to form well-defined nanoparticles. For example, the thiol functionalized nanoparticles served as a multifunctional carrier for dual encapsulation of hydrophobic anticancer drug via physical entrapment and gold nanoparticles (Au NPs) via covalent bonding to the thiol groups. High drug loading and high encapsulation efficiency, along with uniform size distribution and good stability, allow the functionalized nanoparticles to be used for the delivery of anticancer drug and metal nanoparticles, for example in photothermal cancer therapy and biological sensing.

Thus, in a broad aspect, the disclosure provides a biodegradable amphiphilic liquid crystalline copolymer ("copolymer" or "block copolymer") that can readily self-assemble to nanoparticles in aqueous solutions. Thus, in one aspect, the disclosure provides a copolymer comprising:

a first block, which is of formula:

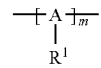

and a second block, which is of formula:

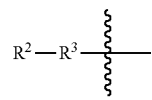

wherein m is an integer about 3 to about 500;

A is independently selected from polyacrylate, polymethacrylate, polynorbonene, polycyclopentene, polycyclooctene, polysiloxane, polyester, or polypeptide;

$R^1$ is a steroid moiety optionally comprising a linker $R^{11}$;

$R^2$ is polyalkylene oxide, polyester, or polypeptide moiety; and $R^3$ is a disulfide linker moiety.

In another aspect, the disclosure provides the block copolymers of the disclosure in a core/shell nanoparticle form. In one embodiment, the core/shell nanoparticle form is wherein the block copolymers of the disclosure self-assembled in aqueous solutions.

In one aspect, the disclosure provides a nanoparticle comprising the block copolymer of the disclosure and a hydrophobic pharmaceutically active molecule. Another aspect provides a therapeutic delivery system comprising this nanoparticle. Yet another aspect provides a method of delivering a pharmaceutically active molecule, comprising administering to a subject this nanoparticle. Yet another aspect provides a method of treating a disease or disorder, comprising administering to a subject this nanoparticle. For example, if the hydrophobic pharmaceutically active molecule is an anti-cancer drug, then the disease or disorder is cancer.

Finally, the disclosure also provides a process for preparing a nanoparticle of the disclosure: comprising (a) dissolving a block copolymer of the disclosure in an organic solvent to obtain a copolymer solution; and (b) mixing the copolymer solution in an aqueous solution to form the nanoparticle.

DETAILED DESCRIPTION OF THE INVENTION

Figure 1:
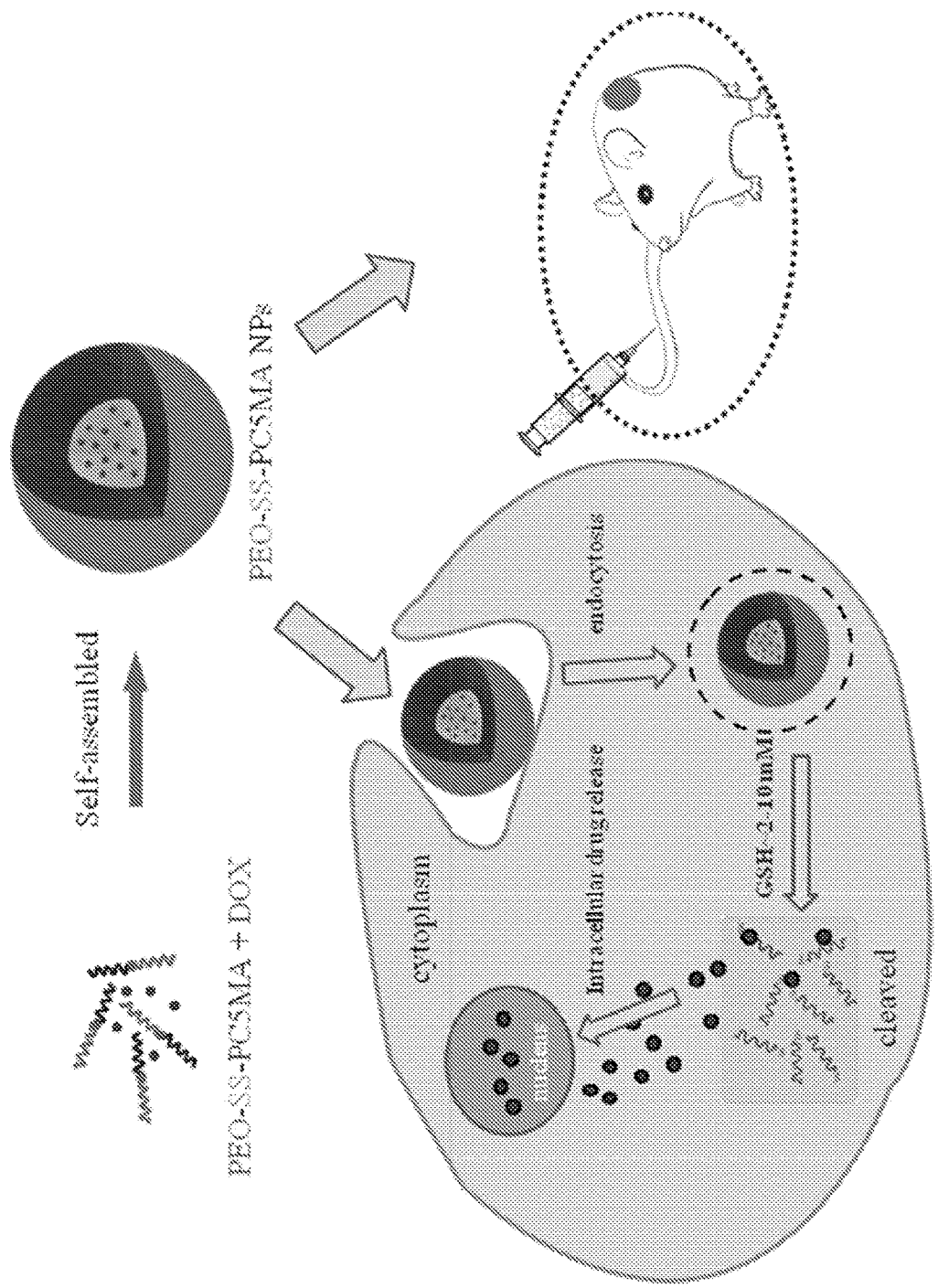
FIG. 1 illustrates reduction-sensitive in aqueous media of PC5MA-SS-PEO NPs for intracellular drug release.
Figure 2:
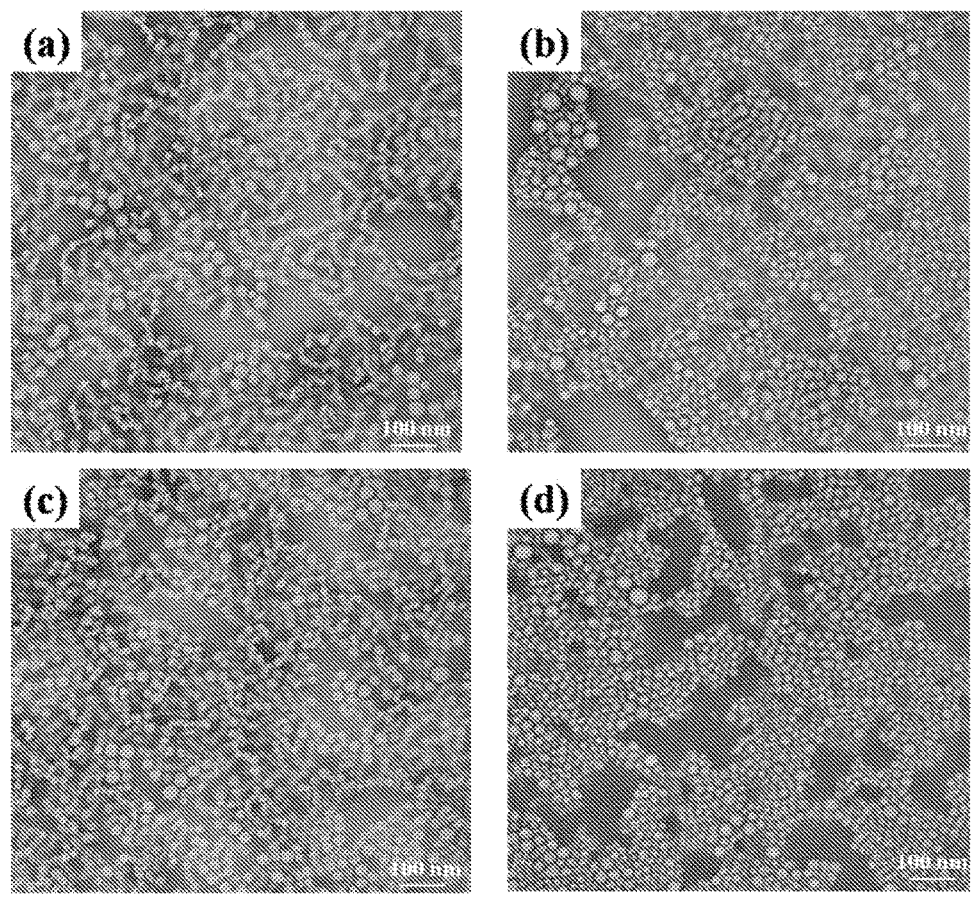
FIG. 2 shows TEM images of (a) blank thioester-NPs, (b) blank SS-NPs, (c) DOX-encapsulated thioester-NPs, and (d) DOX-encapsulated SS-NPs.

Before the disclosed methods and materials are described, it is to be understood that the aspects described herein are not limited to specific embodiments, methods, apparati, or configurations, and as such can, of course, vary. It is also to be understood that the terminology used herein is for the purpose of describing particular aspects only and, unless specifically defined herein, is not intended to be limiting.

In view of the present disclosure, the methods described herein can be configured by the person of ordinary skill in the art to meet the desired need. For example, in certain aspects, the copolymers of disclosure comprise of a steroid-containing block and a polyalkylene oxide-, polyester-, or polypeptide moiety-containing block. Such copolymers readily self-assemble as nanoparticles in aqueous solutions without sonication or homogenization, and have good biocompatibility, high drug loading capacity, long retention in the circulation, multimodality potential and can be easily manufactured in large scale. In another example, the nanostructures of the disclosure may be used to encapsulate a hydrophobic therapeutically active molecule, such as anticancer drugs. The nanoparticles encapsulating anticancer drug showed high tumor accumulation and antitumor efficacy with significantly reduced toxicity compared to the free anticancer drug. In another example, the block copolymers of the disclosure may be functionalized (for example, with thiol), and such copolymers also self-assembled in aqueous media to form well-defined nanoparticles with the functional group. The thiol functionalized nanoparticles served as a multifunctional carrier for dual encapsulation of hydrophobic anticancer drug via physical entrapment and gold nanoparticles (Au NPs) via covalent bonding to the thiol groups. These dual nanoparticles exhibited high drug loading, high encapsulation efficiency, uniform size distribution, and good stability. As a non-reducible control, a copolymer that doesn't contain disulfide bond was also synthesized and compared in vitro and in vivo. Both amphiphilic liquid crystalline polymers self-assembled in aqueous media to form bioreducible and non-reducible nanoparticles. The resulting disulfide-containing nanoparticles of the disclosure possessed enhanced stability under extracellular environment and exhibited rapid drug release under an intracellular reductive condition.

The block copolymers of the disclosure require that the first block comprises a steroid moiety optionally comprising a linker. Suitable steroids may be selected to meet the desired need. For example, the steroid moiety suitable in the materials of the disclosure comprises cholesterol, cholic acid, deoxycholic acid, taurocholic acid, lanosterol, estradiol, testosterone, bile acid, dexamethasone, secosteroid, phytosterol, or the like. In another embodiment, the steroid moiety is selected from cholesterol, cholic acid, deoxycholic acid, and taurocholic acid. In another embodiment, the steroid moiety comprises cholesterol.

The steroid-containing first block may be present from about 1% to about 80% of the total weight of the block copolymer (i.e., weight fraction of about 1% to about 80%.) For example, the weight fraction of the first block may be more that 50%, or less than 50%, or from about 5% to about 70%, or about 40% to about 70%, or about 40% to about 50%, or about 60% to about 70%, or about 2% to about 30%, or about 3% to about 30%, or about 5% to about 30%, or about 2% to about 20%, or about 3% to about 20%, or about 5% to about 20%, or about 7% to about 20%, based on the total weight of the block copolymer.

The steroid moiety may be connected to the polymer back bone via a suitable linker $R^{11}$. Some examples of linker $R^{11}$ include, but are not limited to:

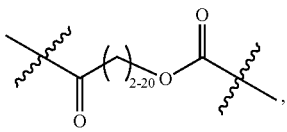

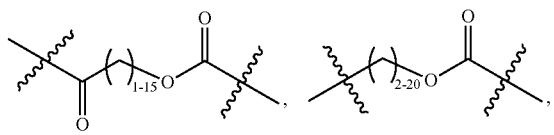

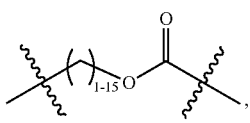

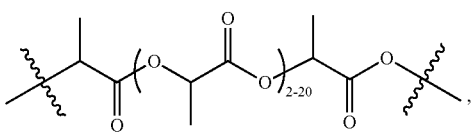

polylactone, or an oligomer of siloxane. In one embodiment, the linker at $R^{11}$ is

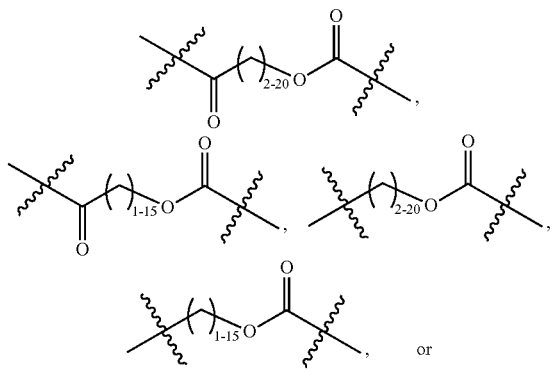

In another embodiment, the linker at $R^{11}$ is:

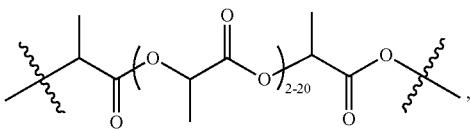

In another embodiment, the linker at $R^{11}$ is

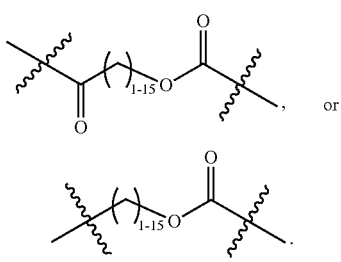

In one embodiment, the linker at $R^{11}$ is

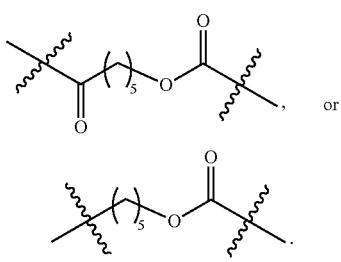

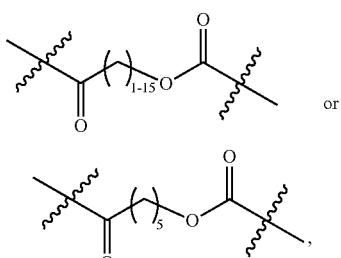

The block copolymers of the disclosure require a backbone moiety A. The block copolymers described herein may contain, for example, polyacrylate, polymethacrylate, polynorbonene, polycyclopentene, polycyclooctene, polysiloxane, polyester, and polypeptide backbone A available to one skill in the art, and may be varied depending on the desired product. In one embodiment, the block copolymers of disclosure are those wherein each A is independently polyacrylate, polymethacrylate, or polyester. In another embodiment, each A is independently polyacrylate or polymethacrylate. In another embodiment, each A is independently polyacrylate. In another embodiment, each A is independently polymethacrylate. In another embodiment, each A is independently polyester.

In an exemplary embodiment, the first block is of formula:

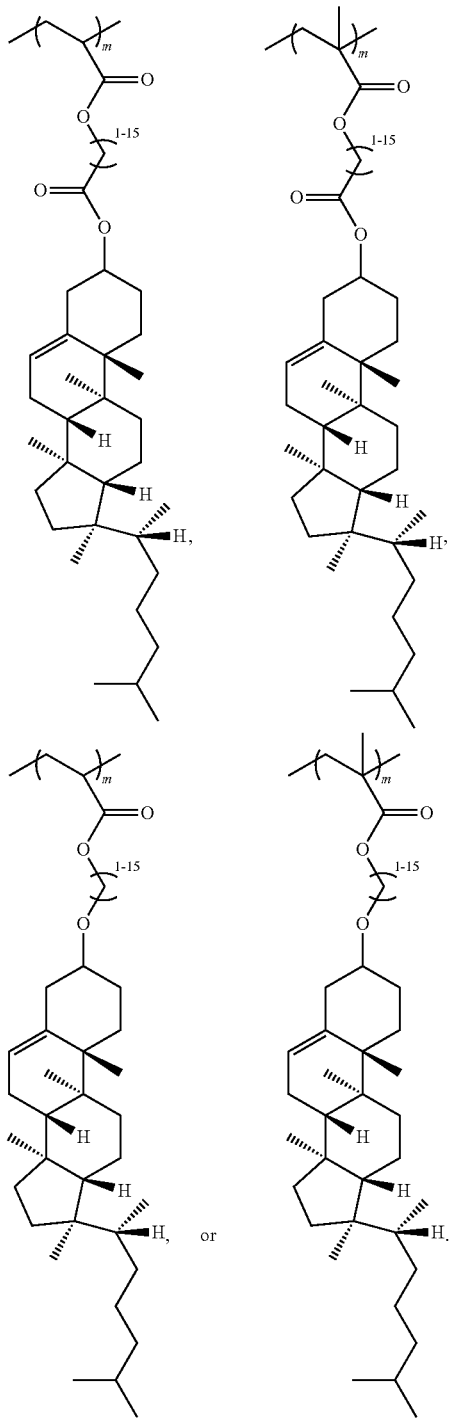

The block copolymers of the disclosure require that the second block is

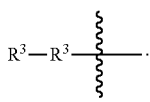

Thus, the second block comprises $R^2$ moiety, which may be polyalkylene oxide, polyester, or polypeptide moiety.

In one embodiment, $R^2$ is polyalkylene oxide moiety. Suitable polyalkylene oxides may be selected to meet the desired need. In some embodiments, the polyalkylene oxide moiety comprises polyethylene oxide, polyethylene oxide thiolate, polypropylene oxide, or polypropylene oxide thiolate. In another embodiment, the polyalkylene oxide moiety comprises polyethylene oxide or polyethylene oxide thiolate. In another embodiment, the polyalkylene oxide moiety comprises polyethylene oxide.

In one embodiment, $R^2$ is polyester moiety. Suitable polyesters include polymers that contain the ester functional group in their main chain. Examples include, but are not limited to, polylactides, polyglycolides, polycaprolactones, and the like.

In one embodiment, $R^2$ is polypeptide moiety. Suitable polypeptides include one or more chains of amino acid monomers linked together by peptide (amide) bonds, and may comprise L-amino acids, D-amino acids (which are resistant to L-amino acid-specific proteases in vivo), or a combination of D- and L-amino acids. Typically, polypeptides described herein refer to a chain less than about 100 amino acids in length. The polypeptides described herein may be chemically synthesized or recombinantly expressed.

The second block may be present from about 20% to about 99% of the total weight of the block copolymer (i.e., weight fraction of about 20% to about 99%.) For example, the weight fraction of the second block may be more that 50%, or less than 50%, or from about 30% to about 95%, or about 30% to about 60%, or about 50% to about 60%, or about 30% to about 40%, or about 70% to about 98%, or about 70% to about 97%, or about 70% to about 95%, or about 80% to about 98%, or about 8% to about 97%, or about 80% to about 95%, or about 80% to about 93%, based on the total weight of the block copolymer.

The second block also comprises $R^3$ linker moiety comprising reducible disulfide bonds. In one embodiment, $R^3$ is selected from the group consisting of:

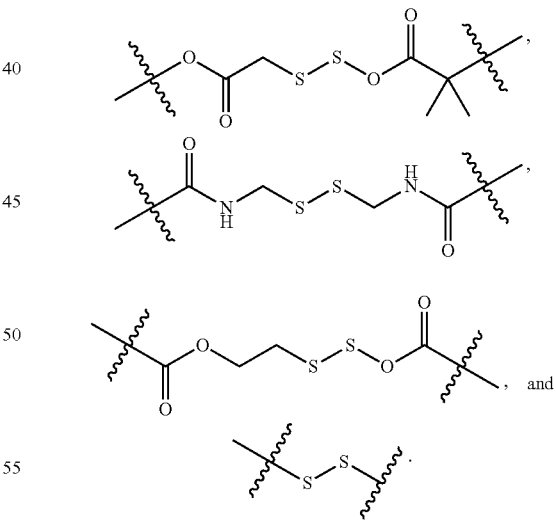

In one embodiment, $R^3$ is

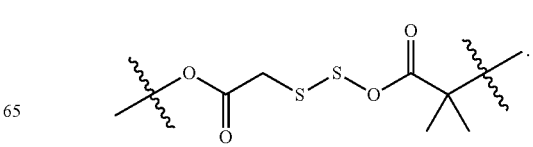

In another embodiment, R³ is derived from

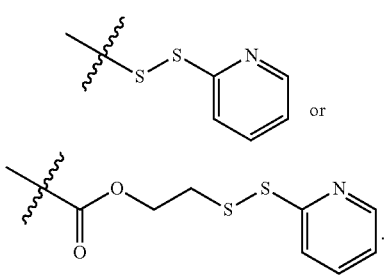

or

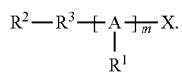

In certain embodiment, the copolymer of the disclosure may further comprise a chain terminus moiety X:

$$R^2-R^3-[A]_m-X.$$
$$\phantom{R^2-R^3-[}R^1$$

In one embodiment, X is a trithiocarbonate, dithiocarbamate, or dithioester. In another embodiment, X is —SC(S)S—($C_1$-$C_{24}$ alkyl). In another embodiment, X is —SC(S)S—$C_{12}H_{25}$.

In one embodiment, the copolymer of the disclosure comprises polyacrylate or polymethacrylate bearing cholesterol block and polyalkylene oxide block with reducible disulfide bonds. In one embodiment, the copolymer of the disclosure comprises polyacrylate or polymethacrylate bearing cholesterol block and polyethylene glycol block with reducible disulfide bonds.

In one embodiment, the block copolymers of the disclosure comprise the structure:

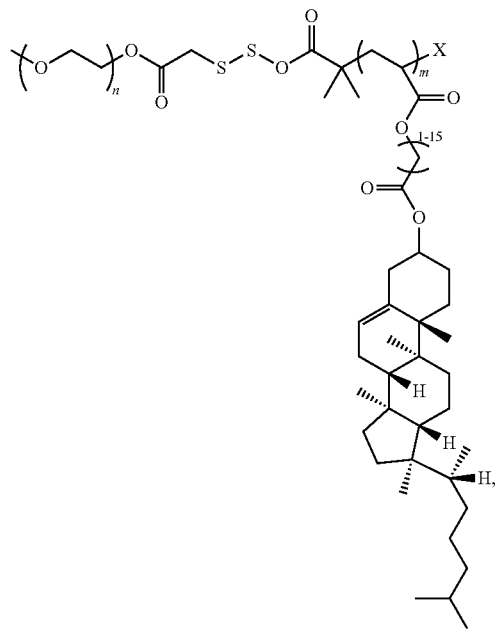

-continued

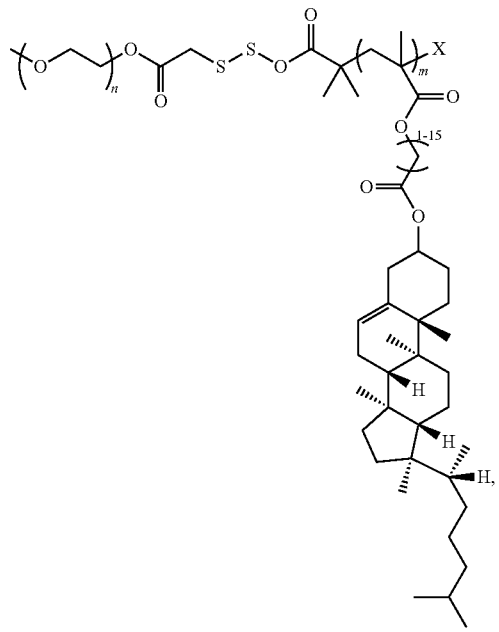

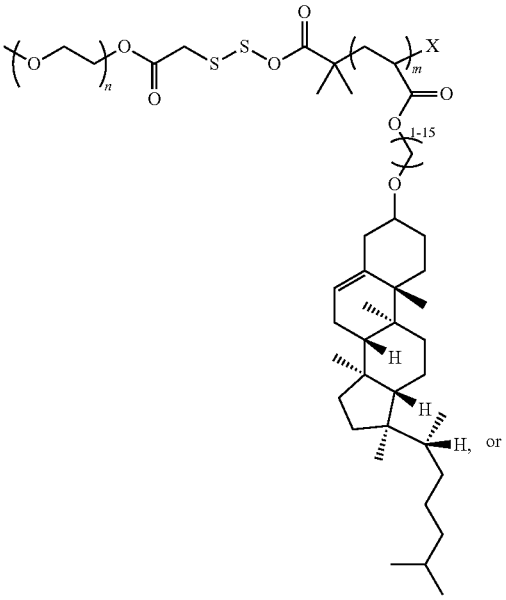

or

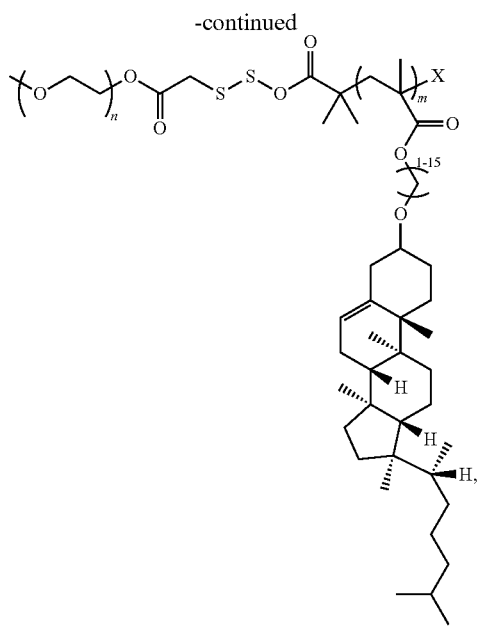

wherein m is an integer between about 5 and about 200; and n is an integer between about 5 and about 100.

The values of m and n may be selected by one of skill in the art and may be varied depending on the desired product. For example, m may be between about 10 and about 100; and/or n may be between about 15 and about 85. The molecular weight of the block copolymer of the disclosure may be between about 5,000 to about 200,000 Da. In one embodiment, the block copolymer of the disclosure is about 5,000 to about 150,000 Da, or about 5,000 to about 100,000 Da, about 5,000 to about 60,000 Da, or about 10,000 to about 150,000 Da, or about 10,000 to about 100,000 Da, or about 10,000 to about 60,000 Da, or about 20,000 to about 150,000 Da, or about 20,000 to about 100,000 Da, or about 20,000 to about 60,000 Da.

The block copolymers of the disclosure may be further comprise one or more additional functional groups. Examples of functional groups include, but are not limited to, thiol, phosphate, carboxylic acid groups, etc. One of skill in the art would be able to select the desired functional group based on the particular application. For example, thiol-functionalized block copolymer may serve as a multifunctional carrier for dual encapsulation of hydrophobic anticancer drug (i.e., via physical entrapment) and gold nanoparticles (Au NPs) via covalent bonding to the thiol groups. Likewise, phosphate- or carboxylic acid-functionalized block copolymer may be used to encapsulate the quantum dots (e.g., CdSe or the like) or magnetic nanoparticles.

The block copolymers disclosed herein have a number of desirable qualities including for example, a relatively low polydispersity. Optionally in embodiments of the invention, the polymer chains exhibit a polydispersity index such that $M_w/M_n$ is between about 1.0 and about 2.5. In some embodiments, the polydispersity index is between about 1.0 and about 2.0, or between about 1.0 and about 1.9, or between about 1.1 and about 1.9, or between about 1.0 and about 1.8, or between about 1.1 and about 1.8, or between about 1.0 and about 1.5, or between about 1.5 and about 1.5, or between about 1.0 and about 1.3, or between about 1.0 and about 1.2, or about 1.0, or about 1.1, or about 1.2, or about 1.3, or about 1.4, or about 1.5, or about 1.6, or about 1.7, or about 1.8, or about 1.9, or even about 2.0. In certain embodiments, the polymer exhibits a polydispersity of $M_w/M_n$ between about 1.0 and about 1.5. In some other embodiments, the polymer exhibits a polydispersity of $M_w/M_n$ between about 1.0 and about 1.2.

The copolymers of the disclosure, in one aspect, may be present in a nanoparticle form (e.g., core/shell nanoparticle form). In one embodiment, the core/shell nanoparticle form is wherein the block copolymers of the disclosure self-assembled in aqueous solutions. Such nanoparticles are able to encapsulate large amount of hydrophobic drug molecules into the nanoparticles during the self-assembling process. Thus, in one aspect, the disclosure provides a nanoparticulate system for drug delivery using the amphiphilic copolymers of the disclosure. In one aspect, the disclosure provides a nanoparticle comprising the block copolymer of the disclosure and a hydrophobic pharmaceutically active molecule. Any suitable hydrophobic pharmaceutically active molecule may be used depending on the desired therapeutic effect. Some examples include, but are not limited to doxorubicin, daunorubicin, vincristin, paclitaxel, docetaxel, cisplatin, camptothecin, irinotecan, 5-fluorouracil, methotrexate, or dexamethasone.

The nanoparticles of the disclosure may further comprise one or more of metal nanoparticles, such as gold nanoparticles and/or magnetic nanoparticles and/or quantum dots (for example, near infrared (NIR) quantum dot, CdSe and the like.).

The block copolymers disclosed herein have a number of desirable qualities including for example, well-defined with uniform size distribution. The nanoparticles of the disclosure may be anywhere from about 5 to about 900 nm in size. For example, the nanoparticles may be between about 5 and about 200 nm, or between about 10 and about 100 nm, or between about 10 and about 200 nm, or between about 50 and about 150 nm, or between about 100 and about 250 nm, or between about 100 and about 200 nm, or between about 120 and about 150 nm, or between about 110 and about 150 nm, or between about 120 and about 180 nm, or between about 150 and about 250 nm, or between about 150 and about 200 nm.

The disclosure also provides methods for preparing the nanoparticles of the disclosure, comprising: (a) dissolving the copolymer of any one of the claims in an organic solvent to obtain the copolymer solution; and (b) mixing the copolymer solution in an aqueous solution to form a nanoparticle. Organic solvent suitable in preparation of the nanoparticles include, but are not limited to, dimethylformamide, dimethyl sulfoxide, dioxane, tetrahydrofurane, or any combination thereof. Mixing the copolymer solution may be performed by dialysis in the aqueous solution.

Definitions

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. In some embodiments, the term "about" means±10% of the recited value. In another embodiment, term "about" means±5% of the recited value.

As used herein the term "combining" includes adding one or more items to a reaction mixture.

As used herein the term "dispersity," "polydispersity," "polydispersity index", "PDI," and "$M_w/M_n$" are used interchangeably and refer to measure of the polymer uniformity with respect to distribution of molecular mass. The dispersity may be calculated by dividing weight average molecular weight ($M_w$) by the number average molecular weight ($M_n$) (i.e., $M_w/M_n$). In certain embodiments, the dispersity may be calculated according to degree of polymerization, where the dispersity equals $X_w/X_n$, where $X_w$ is the weight-average degree of polymerization and $X_n$ is the number-average degree of polymerization.

All percentages, ratios and proportions herein are by weight, unless otherwise specified. A weight percent (weight %, also as wt %) of a component, unless specifically stated to the contrary, is based on the total weight of the composition in which the component is included (e.g., on the total amount of the reaction mixture).

EXAMPLES

The materials and methods of the disclosure are illustrated further by the following examples, which are not to be construed as limiting the disclosure in scope or spirit to the specific procedures and materials described in them.

Materials and Methods

Doxorubicin hydrochloride (DOX.HCl) was purchased from Biotang Inc (Waltham, Mass., USA). D,L-dithiothreitol (DTT), thioglycolic acid (98%), p-toluenesulfonic acid monohydrate (PTSA), N,N'-dicyclohexylcarbodiimide (DCC), 4-(dimethylamino)pyridine (DMAP), pyrene and other conventional reagents were obtained from Sigma-Aldrich Chemical Co. (St. Louis, Mo., USA). Triethylamine (TEA) and dimethyl formamide (DMF) were purchased from Fisher Scientific (Boston, Mass., USA). Penicillin-streptomycin, 0.25% (w/v) trypsine-0.03% (w/v) EDTA solution, RPMI 1640, and DMEM medium were purchased from American Type Culture Collection (Rockville, Md., USA). Mouse fibroblasts (NIH3T3) and human lung cancer cell lines (A549) were purchased from the National Cancer Institute (Frederick, Md., USA). Fetal bovine serum (FBS) was purchased from Atlanta Biologicals (Norcross, Ga., USA). 1,1'-Dioctadecyl-3,3,3',3'-tetramethylindotricarbocyanine iodide (DiR) and in vitro toxicology assay kits (MTT based) were obtained from Invitrogen (Carlsbad, Calif., USA). Spectra/Pro membranes were purchased from Spectrum Laboratories, Inc. (Rancho Dominguez, Calif., USA). All chemicals were analytical grade and used without purification. The liquid crystalline monomer, cholesteryl 6-methacryloyloxyhexaneoate (C5MA), was prepared according to Hamley et al. (*Soft Matter.* 2005; 1:355-363.) The RAFT agent S-1-dodecyl-S'— (α,α'-dimethyl-acetic acid) trithiocarbonate (CTA) was synthesized according to Lai et al. (*Macromolecules.* 2002; 35:6754-6756).

Data is expressed as mean±standard deviation. The statistical significance of difference between experimental and control groups was determined using a student's t-test. A probability (p) of less than 0.05 was considered statistically significant.

Example 1: Synthesis and Purification of Cholesterol-Based Block Copolymer with Disulfide Linkage PEO-SS-PC5MA

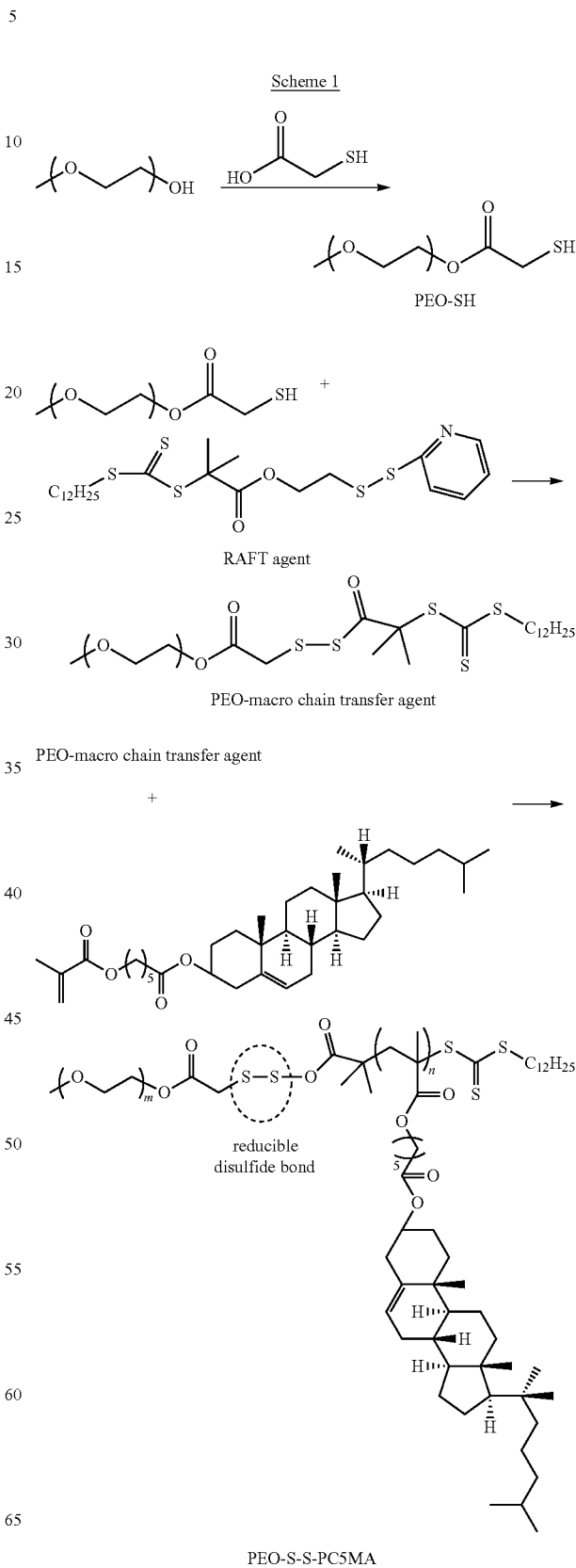

Raft Agent:

Hydroxy-mercaptopyridine (2.52 g, 13.46 mmol) was dissolved in 50 mL of dichloromethane and S-dodecyl-S'-2-(2,2-dimethylacetic acid) trithiocarbonate (3.62 g, 11.21 mmol) was added to this solution. DCC (2.78 g, 13.46 mmol) and DMAP (0.4 g, 3.36 mmol) were subsequently added to this mixture and the solution was stirred for 12 h at room temperature. After evaporating the solvent, the crude reaction mixture was purifiedby column chromatography using silica gel as the stationary phase and mixture of ethylacetate/hexane (4:1 v/v ratio) as eluent to yield 4.4 g (83%) of RAFT agent as a yellow liquid. $^1$HNMR (CDCl$_3$, ppm) δ: 8.41 (d, 1H), 7.70-7.62 (m, 2H), 7.03 (t, 1H), 4.32 (t, 2H), 3.22 (t, 2H), 3.00 (t, 2H) 1.67-1.60 (m, 8H), 1.33-1.21 (m, 18H), 0.84 (t, 3H); $^{13}$C-NMR (CDCl3, ppm) δ: 172.7, 159.9, 149.6, 137.1, 120.8, 119.7, 63.3, 55.8, 37.2, 37.0, 31.9, 29.6, 29.5, 29.4, 29.3, 29.1, 28.9, 27.9, 25.3, 22.7, 14.2.

PEO-SH:

Methoxypolyethylene glycol 20000 (5.0 g, 0.25 mmol) and PTSA (17 mg, 0.01 mmol) were added to a round bottom flask in freshly distilled toluene. To this solution, thioglycolic acid (150 mg, 1.0 mmol) was then added slowly. The solution was then refluxed under Ar atmosphere overnight. The reaction mixture was cooled down and concentrated under vacuumn. The residue was partitioned using dicholoromethane/water, and the organic layer was dried over MgSO$_4$. The organic layer was collected and concentrated. The crude product was then dissolved in 20 mL of methanol followed by adding DTT (303 mg, 2.0 mmol) to reduce the possibility of forming disulfide. The solution was stirred for 3 h at room temperature. The resulting solution was poured in diethylether to precipitate the product PEO-SH, which was washed 5 times with ether to remove DTT. 4.0 g of the pure product was obtained as white solid in 80% yield. GPC (THF) $M_n$: 20250. PDI: 1.06, $^1$H NMR (400 MHz, CDCl$_3$) δ: 4.27 (t, 2H, —COOCH$_2$—, in PEO end group), 3.79-3.44 (m, —CH$_2$CH$_2$O—, repeating units of PEO), 3.35 (s, —OCH$_3$); $^{13}$C NMR (CDCl$_3$) δ: 170.9 (—COO), 70.3, 64.8, 59.7 (—CH$_2$ repeat unit in PEO).

PEO Macro Chain Transfer Agent:

RAFT agent (3.0 g, 5.62 mmol), PEO-SH (4.5 g, 0.25 mmol), and 0.5 mL glacial acetic acid were dissolved in methanol (50 mL) and the reaction mixture was stirred at room temperature for 6 h under nitrogen atmosphere. The reaction was stopped and the solvent was evaporated. The crude PEO macro chain transfer agent product was purifiedby column chromatography using silica gel as stationary phase and mixture of ethylacetate/hexane (4:1 v/v ratio) and methylene chloride/methanol (4:1 v/v ratio) as eluents. 5.8 g of the pure was obtained as light yellow solid in 76% yield. GPC (THF) $M_n$: 20 400. PDI: 1.12. $^1$H NMR (400 MHz, CDCl$_3$) δ: 4.26-4.19 (m, 4H, —COOCH$_2$—, in PEO end group), 3.80-3.42 (m, —CH$_2$CH$_2$O—, repeating units of PEO). 3.35 (s, —OCH$_3$), 3.22 (t, CH$_3$C$_{10}$H$_{20}$CH$_2$—S—), 1.67-1.60 (m, —S—C(CH$_3$)$_2$COO—), 1.33-1.21 (m, CH$_3$C$_{10}$H$_{20}$CH$_2$S—), 0.84 (t, CH$_3$C$_{10}$H$_{20}$CH$_2$S—); $^{13}$C NMR (CDCl$_3$) δ: 172.6, 169.4, 70.8, 70.4, 68.8, 64.6, 63.4, 62.1, 58.9, 55.8, 53.4, 41.5, 36.9, 36.5, 31.8, 29.5, 29.3, 29.0, 27.8, 25.3, 22.6, 21.2, 14.1.

PEO-SS-PC5MA:

In a representative procedure, mixture of the PEO macro chain transfer agent (1.2 g, 0.2 mmol), C5MA (3.8 g, 28.0 mmol), and AIBN (6 mg, 0.04 mmol) were dissolved in 1,4-dioxane (3 mL) and degassed by performing three freeze-evacuate-thaw cycles. The reaction mixture was sealed and then placed in an oil bath maintained at 90° C. for 20 h. The resulting mixture was concentrated and precipitated in a large excess of methanol. The crude product was collected, Soxhlet extracted overnight using methanol to remove unreacted monomer, then extracted with THF and reprecipitated into methanol. The product, PEO-SS-PC5MA, was collected and dried under vacuum. $^1$H NMR (CDCl$_3$, δ ppm): 5.33 (d, 1H, —C=CH—, olefin group in cholesteryl moiety), 4.5 (m, 1H, —CH$_2$—COO—CH), 3.9 (m, 2H, —COOCH$_2$CH$_2$), 3.64 (m, —CH$_2$CH$_2$O— repeating units of PEO), 3.45 (m, 2H, —CH$_2$OCH—), 3.36 (s, —OCH$_3$), 3.2 (t, 2H, CH$_3$C$_{10}$H$_{20}$CH$_2$—S—), 2.50-0.55 (m, —CH$_3$, —CH$_2$—, —CH—, —CH—(CH$_3$)— in cholesteryl moiety, —CH$_2$—C(CH$_3$)COO—, —CH$_2$CH$_2$—CH$_2$CH$_2$CH$_2$— in spacer). $^{13}$C NMR (CDCl$_3$, δ ppm): 170.9 (—COO), 140.9 (—C=CH—, olefin group in cholesterol), 121.9 (—C=CH—, olefin group in cholesterol), 133, 126.6 (—CH$_2$, CH in vinyl group), 74.5 (—COOCH), 70.3 and 64.8 (—CH$_2$ repeat unit in PEO), 51.3-11.2 (—CH$_2$—C(CH3)COO—, -cholesterol).

The detailed chemical structure of as-synthesized PEO-SS-PC5MA was confirmed by $^1$H-NMR. The $^1$H-NMR allowed the determination of molar composition and molecular weight of the obtained block copolymer. The signals at 5.3, 3.9 and 2.5-0.55 ppm were attributed to the protons of cholesterol. Additionally, monomer olefin peaks at 6.42, 6.09 and 5.54 ppm were absent in PEO-SS-PC5MA. The signals of the PEO block corresponding to the PEO repeating unit and the methylene end groups of PEO were observed at 3.6 ppm and 4.25 ppm, respectively. By comparing the integration of peaks in the $^1$H-NMR spectra at 5.33 ppm (olefin group in cholesteryl moiety) and 3.64 ppm (PEO) repeating unit), the weight fraction of the each block was determined. Gel permeation chromatography (GPC) was used to measure the number average molecular ($M_n$) and the polydispersity indices (PDI) of PEO-SS-PC5MA (Table 1).

TABLE 1

Molecular characterization of as-synthesized polymers

| Polymer | $M_n$ (g/mol) GPC[a] | PDI[a] | Weight fraction[b] (%) PEO | PC5MA | Conversion[c] (%) |
|---|---|---|---|---|---|
| PEO-SH | 20 250 | 1.05 | 100 | — | 85 |
| PEO macro chain transfer agent | 20 500 | 1.12 | 100 | — | 92 |
| PEO-SS-PC5MA | 38 250 | 1.13 | 60 | 40 | 90 |
| PEO-PC5MA-thioester | 37 600 | 1.16 | 60 | 40 | 88 |

[a] Determined by GPC calibrated at 40° C. with THF as the mobile phase with polystrene standards.
[b] The ratio of the integrals of peaks by $^1$H-NMR spectra at 5.33 ppm (olefin group in cholesteryl moiety) and 3.64 ppm (PEO repeating unit) is used to calculate the weight fraction of the brush-chol-BCPs.
[c] Conversion of monomer to polymerwas determined using $^1$H NMR analysis

Example 2: Synthesis and Purification of Cholesterol-Based Block Copolymer Without Disulfide Linkage PEO-PC5MA

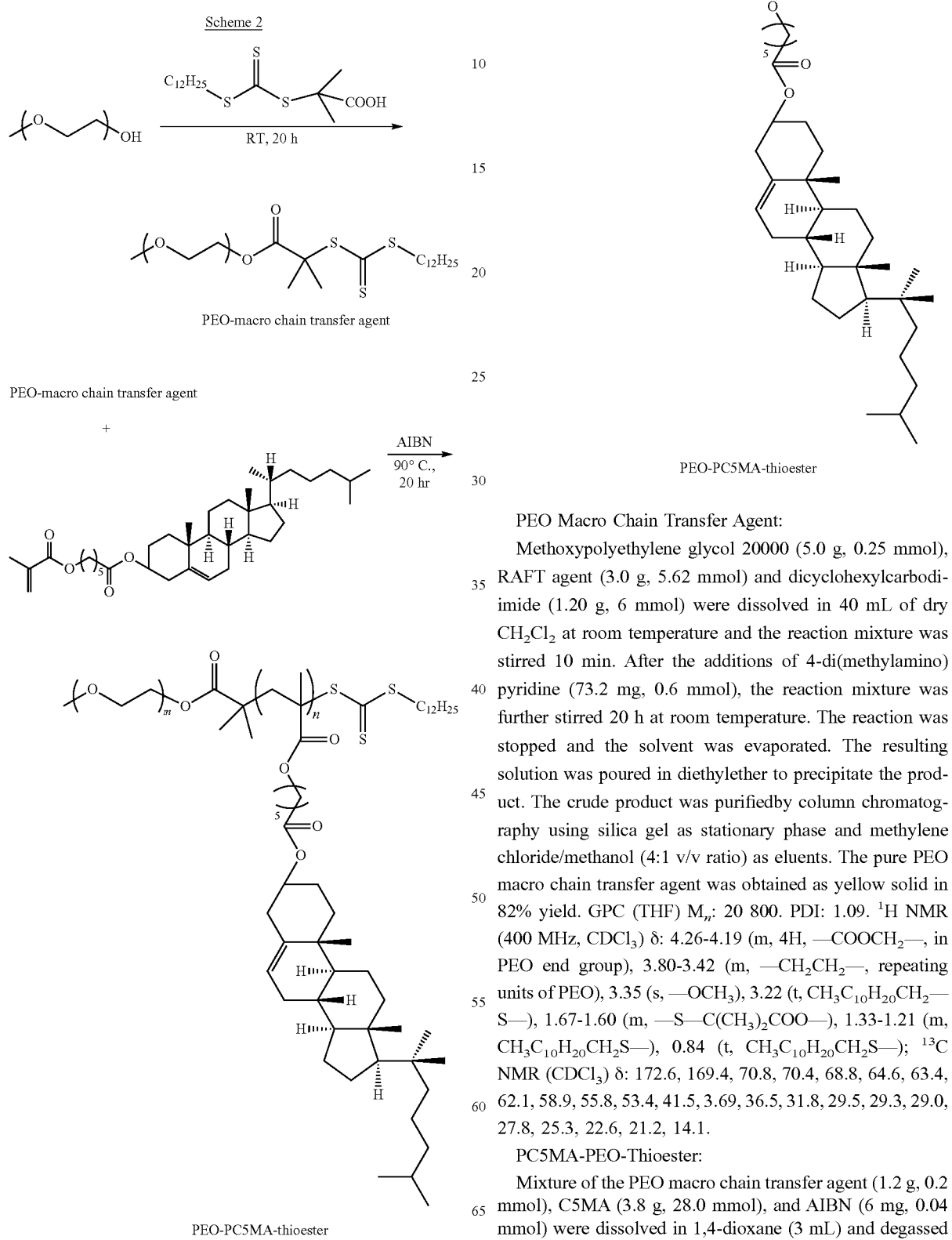

PEO Macro Chain Transfer Agent:

Methoxypolyethylene glycol 20000 (5.0 g, 0.25 mmol), RAFT agent (3.0 g, 5.62 mmol) and dicyclohexylcarbodiimide (1.20 g, 6 mmol) were dissolved in 40 mL of dry $CH_2Cl_2$ at room temperature and the reaction mixture was stirred 10 min. After the additions of 4-di(methylamino)pyridine (73.2 mg, 0.6 mmol), the reaction mixture was further stirred 20 h at room temperature. The reaction was stopped and the solvent was evaporated. The resulting solution was poured in diethylether to precipitate the product. The crude product was purifiedby column chromatography using silica gel as stationary phase and methylene chloride/methanol (4:1 v/v ratio) as eluents. The pure PEO macro chain transfer agent was obtained as yellow solid in 82% yield. GPC (THF) $M_n$: 20 800. PDI: 1.09. $^1$H NMR (400 MHz, $CDCl_3$) δ: 4.26-4.19 (m, 4H, —$COOCH_2$—, in PEO end group), 3.80-3.42 (m, —$CH_2CH_2$—, repeating units of PEO), 3.35 (s, —$OCH_3$), 3.22 (t, $CH_3C_{10}H_{20}CH_2$—S—), 1.67-1.60 (m, —S—$C(CH_3)_2COO$—), 1.33-1.21 (m, $CH_3C_{10}H_{20}CH_2S$—), 0.84 (t, $CH_3C_{10}H_{20}CH_2S$—); $^{13}$C NMR ($CDCl_3$) δ: 172.6, 169.4, 70.8, 70.4, 68.8, 64.6, 63.4, 62.1, 58.9, 55.8, 53.4, 41.5, 3.69, 36.5, 31.8, 29.5, 29.3, 29.0, 27.8, 25.3, 22.6, 21.2, 14.1.

PC5MA-PEO-Thioester:

Mixture of the PEO macro chain transfer agent (1.2 g, 0.2 mmol), C5MA (3.8 g, 28.0 mmol), and AIBN (6 mg, 0.04 mmol) were dissolved in 1,4-dioxane (3 mL) and degassed by performing three freeze-evacuate-thaw cycles. The reaction mixture was sealed and then placed in an oil bath maintained at 90° C. for 20 h. The resulting mixture was concentrated and precipitated in a large excess of methanol. The crude product was collected, Soxhlet extracted overnight using methanol to remove unreacted monomer, then extracted with THF and reprecipitated into methanol. The product, PC5MA-PEO-thioester, was collected and dried under vacuum. The thioester peak was appeared at 310 nm, as measured by UV-visible spectroscopy. $^1$H NMR (CDCl$_3$, δ ppm): 5.33 (d, 1H, —C=CH—, olefin group in cholesteryl moiety), 4.5 (m, 1H, —CH$_2$—COO—CH), 3.9 (m, 2H, —COOCH$_2$CH$_2$), 3.64 (m, —CH$_2$CH$_2$O— repeating units of PEO), 3.45 (m, 2H, —CH$_2$OCH—), 3.36 (s, —OCH$_3$), 3.2 (t, 2H, CH$_3$C$_{10}$H$_{20}$CH$_2$—S—), 2.50-0.55 (m, —CH$_3$, —CH$_2$—, —CH—, —CH—(CH$_3$)— in cholesteryl moiety, —CH$_2$—C(CH$_3$)COO—, —CH$_2$CH$_2$—CH$_2$CH$_2$CH$_2$— in spacer). $^{13}$C NMR (CDCl$_3$, δ ppm): 170.9 (—COO), 140.9 (—C=CH—, olefin group in cholesterol), 121.9 (—C=CH—, olefin group in cholesterol), 133, 126.6 (—CH$_2$, CH in vinyl group), 74.5 (—COOCH), 70.3 and 64.8 (—CH$_2$ repeat unit in PEO), 51.3-11.2 (—CH$_2$—C(CH3)COO—, -cholesterol). GPC (40° C. THF mobile phase, polystyrene standards): M$_n$=39 600 g/mol, PDI=1.17.

Example 3: Preparation and Characterization of Self-Assembled Nanoparticles and Dox-Nps Blank self-assembled NPs were prepared by a dialysis method. Briefly, PC5MA-SS-PEO or PC5MA-PEO-thioester was dissolved in DMF with the aid of sonication. The solution was then transferred to a dialysis bag (MWCO: 10,000 Da) and dialyzed against distilled water for 48 h. To prepare DOX-loaded SS-NPs and thioester-NPs, DOX.HCl was first dissolved in DMF containing 2 equivalents of triethylamine (TEA) and stirred overnight in the dark to form hydrophobic DOX and TEN.HCl. Each copolymer was added, and then the solution was stirred for another 1 h in the dark. The solution was then dialyzed against distilled water for 48 h to remove solvents. Since DOX is hydrophobic with limited solubility, un-encapsulated DOX beyond the solubility will precipate in water. The precipitated DOX was removed by centrifugation at 8000 rpm for 10 min, followed by filtration through 0.45 μm syringe to collect clear red solution of DOX-encapsulated nanoparticles. The final products were collected after lyophilization.

The average particle size, size distribution and zeta-potential of the DOX-loaded SS or thioester NPs (1 mg/mL) were measured using a dynamic light scattering (DLS) instrument (Malvern Zetasizer). The morphologies of DOX-loaded SS or thioester NPs were imaged by TEM (FEI Tecnai Biotwin, Eindhoven, Netherlands). Specimens were prepared by adding a suspension of the nanoparticles dropwise to a Formvar/carbon film grid followed by air-drying.

The Critical Aggregation Concentration (CAC) of PC5MA-SS-PEO or PC5MA-PEO-thioester copolymers was determined by fluorescence measurements using pyrene as a hydrophobic probe. Pyrene solutions (3×10$^{-4}$ M) in acetone were added to glass tubes and were subsequently evaporated to remove the organic solvent. Various concentrations of copolymer solutions (10 mL) were added to the tubes and sonicated for 3 h at 60° C. to equilibrate the pyrene and the nanoparticles. The copolymer concentrations ranged from 0.005 to 0.5 mg/mL and the final concentration of pyrene was 6.0×10$^{-7}$ M. The emission spectra of pyrene were recorded from 350-450 nm using a fluorescence spectrophotometer (Perkin Elmer LS-55B, USA) at an excitation wavelength of 336 nm. For the measurement of the intensity ratio of the first (374.5 nm) and the third highest energy bands (386 nm) in the pyrene emission spectra, the slit opening for the excitation and emission spectra was set at 5 nm.

The amount of DOX-encapsulated into nanoparticles was determined by a colorimetric method. The lyophilized DOX-loaded SS or thioester NPs (0.5 mg) were dissolved in DMF (2 mL) to obtain clear solutions. The absorbance at 480 nm was detected with a UV-VIS spectrophotometer (Shimadzu, Japan). DOX solutions were prepared at various concentrations and the absorbance at 480 nm was measured to generate a calibration curve for calculating drug-loading content. The drug-loading content (DLC) and encapsulation efficiency (EE) were calculated using the following equations:

$$DLC = \frac{\text{Amount of } DOX \text{ in nanoparticles}}{\text{Amount of } DOX - \text{loaded nanoparticles}} \times 100$$

$$EE = \frac{\text{Amount of } DOX \text{ in nanoparticles}}{\text{Amount of } DOX \text{ used for nanoparticle preparation}} \times 100$$

The self-assembly behavior of the PC5MA-SS-PEO copolymers in aqueous solution was characterized by measuring the critical micelle concentration (CMC) using pyrene as a hydrophobic fluorescence probe. The CMC value of the PC5MA-SS-PEO copolymer (11.4±0.1 mg/L) was slightly lower than that of the PC5MA-PEO-thioester copolymer (13.1±0.3 mg/L) (Table 2).

TABLE 2

Characterization of self-assembled blank nanoparticles and DOX-encapsulated nanoparticles

| Samples | CMC (mg/L) | DOX•HCl feed ratio (%) | DLC (%) | EE (%) |
|---|---|---|---|---|
| Blank SS-NPs | 11.4 ± 0.1 | | | |
| Blank SH-NPs | 13.1 ± 0.3 | | | |
| DOX-encapsulated SS-NPs | | 20 | 18.2 | 94.5 |
| DOX-encapsulated thioester-NPs | | 20 | 17.1 | 88.1 |

| Samples | Average size (nm) | PDI | Zeta potential (mV) |
|---|---|---|---|
| Blank SS-NPs | 85.1 ± 3.1 | 0.16 | −25.1 ± 0.4 |
| Blank SH-NPs | 92.3 ± 4.2 | 0.12 | −28.3 ± 0.2 |
| DOX-encapsulated SS-NPs | 89.4 ± 5.4 | 0.17 | −23.4 ± 0.6 |
| DOX-encapsulated thioester-NPs | 101.3 ± 8.9 | 0.19 | −22.1 ± 0.3 |

CMC: critical micelle concentration, measured by the probe fluorescence technique
DLC: drug loading content = (amount of DOX in nanoparticle/amount of DOX-loaded nanoparticle) × 100
EE: encapsulation efficiency = (amount of DOX in nanoparticle/amount of DOX used for nanoparticle preparation) × 100

The hydrophobic DOX was encapsulated into the PC5MA-SS-PEO and PC5MA-PEO-thioester self-assembled NPs through hydrophobic interactions between DOX and cholesterol moieties. With a DOX.HCl feed ratio of 20% (w/w), the drug loading content (DLC) in the PC5MA-PEO-thioester NPs was about 17.1% with encapsulation efficiency (EE) of 88.1%. The DLC and EE values were slightly higher in the PC5MA-SS-PEO copolymer (18.2% w/w and 94.9%, respectively) (Table 2). The size and morphology of blank PC5MA-SS-PEO NPs, blank PC5MA-PEO-thioester NPs, DOX-encapsulated PC5MA-SS-PEO NPs, and DOX-encapsulated PC5MA-PEO-thioester NPs were examined by TEM (FIG. 2) and dynamic light scattering (DLS) (Table 2), respectively. The TEM images showed that all the self-assembled nanoparticles were spherical in shape with sizes of 20-40 nm (FIG. 2a-d). The average particle size of blank PC5MA-SS-PEONPs and blank PC5MA-PEO-thioester NPs measured by DLS was about 85.1 nm and 92.3 nm, respectively with narrow size distribution (PDI less than 0.2) (Table 2). These were larger than the sizes measured by TEM, which might be due to the existence of the self-assembled NPs in a swollen state in aqueous media. Encapsulation of DOX slightly increased the particle size of the nanoparticles to 89.4 nm in DOX-encapsulated PC5MA-SS-PEO NPs, and 101.3 nm in DOX-encapsulated PC5MA-PEO-thioester NPs. The SS-NPs, thioester-NPs, and DOX-loaded NPs were negatively charged at their surface as reflected by zeta potential values in the range of −22 mV to −26 mV. The physical loading of DOX slightly decreased the negative surface charge of the nanoparticles.

Figure 3:
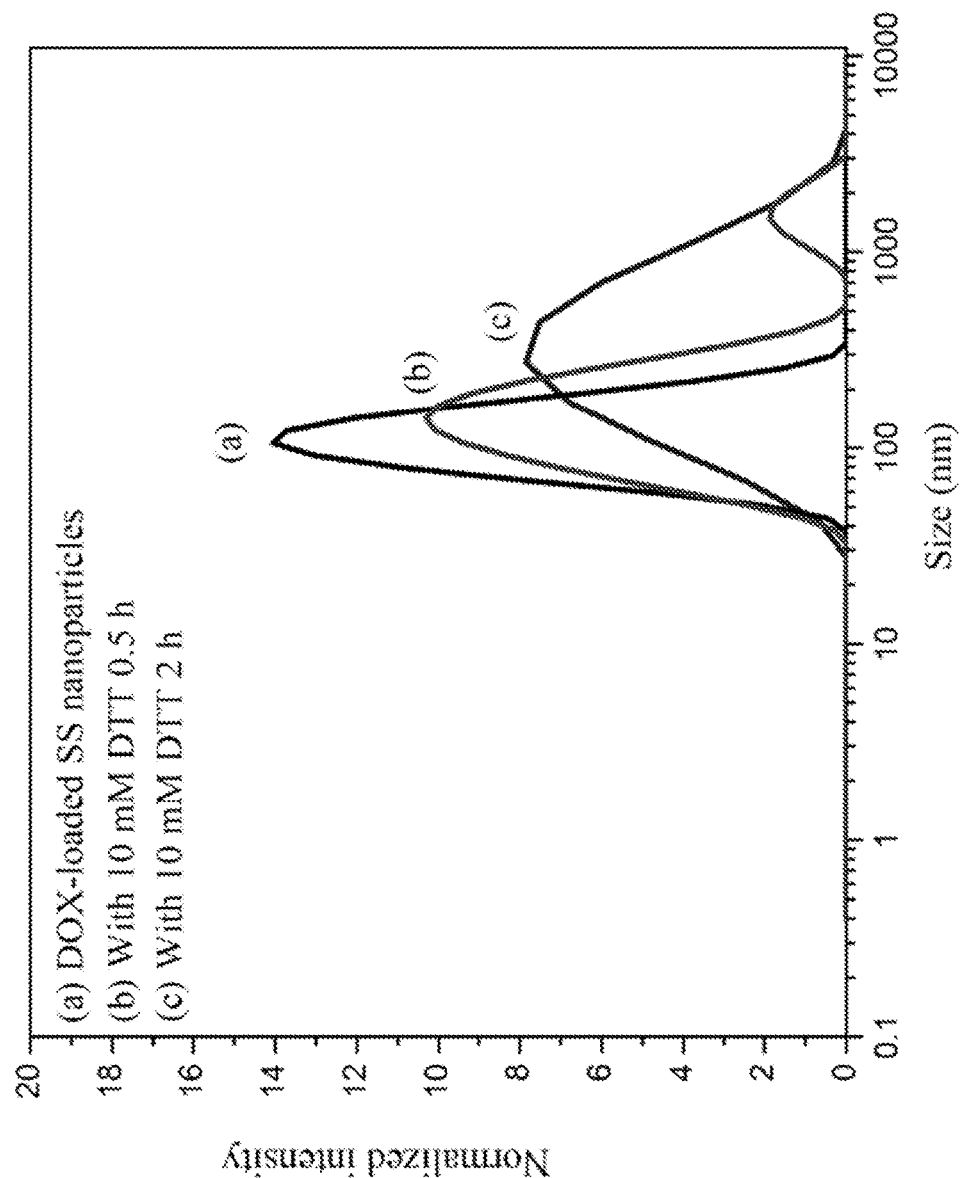
FIG. 3 shows the particle size distribution of PC5MA-SS-PEO NPs after incubation with or without 10 mM of DTT solution.

To observe reduction-triggered destabilization, the PC5MA-SS-PEO NPs were incubated with 10 mM DTT in PBS buffer (pH 7.4, 10 mM) at 37° C. with shaking, and the size change of the NPs was examined at different time intervals. An increase in the size of the PC5MA-SS-PEO NPs with the appearance of two peaks was observed at 30 min incubation with DTT (FIG. 3). The initial size of PC5MA-SS-PEO NPs displayed a unimodal distribution with an average hydrodynamic diameter of 85.1±3.1 nm. However, the particles size of the NPs dramatically increased to 235 nm after 30 min and to 540 nm after 2 h incubation with DTT. After 4 h of incubation with DTT, no particle size was measurable, indicating completed dissociation of the SS-NPs.

Example 4: Stability of DOX-Encapsulated NPs

Lyophilized DOX-loaded SS or thioester NPs (1 mg/mL) were suspended in the serum-containing phosphate-buffered saline (PBS) solution (50% FBS), followed by sonication for 10 min and filtration through a 0.45 μm syringe filter membrane. The particle size of the nanoparticles stored at 4° C. was monitored over the storage time using a Malvern Zetasizer. Reduction-triggered destabilization of DOX-encapsulated SS-NPs was observed by detecting the change in size of the NPs in responseto 10 mM DTT in aqueous medium. Briefly, DOX-encapsulated SS-NPs were dissolved in 10 mM DTT containing PBS at a concentration of 1 mg/mL and then kept in a shaking bath at 37° C. The particle size was measured by DLS at a pre-determined time. The average particle size of the DOX-encapsulated PC5MA-SS-PEO NPs and PC5MA-PEO-thioester NPs did not change significantly after 1 week storage at 4° C. in 50% FBS (FIG. 4a), and no precipitation or aggregation was observed.

Example 5: Reduction-Triggered Release of DOX from the SS or Thioester NPs

In vitro release of DOX from the nanoparticles was studied using a dialysis method. Briefly, lyophilized DOX-loaded NPs (6 mg) were suspended in 3 mL of PBS (0.01 M, pH 7.4), followed by sonication for 10 min to yield an optically clear suspension. The suspensions were introduced into 5 mL-dialyzers (MWCO: 10,000 Da) and immersed in 20 mL of PBS or PBS containing 10 mM DTT at 37° C. in a shaking bath at 100 rpm. At selected time intervals, aliquots (10 mL) were removed from the dissolution medium and an equivalent volume of fresh medium was compensated. The concentration of DOX was immediately measured by UV at 480 nm. The percentage of DOX released was calculated based on a standard curve of known DOX concentrations.

Figure 4:
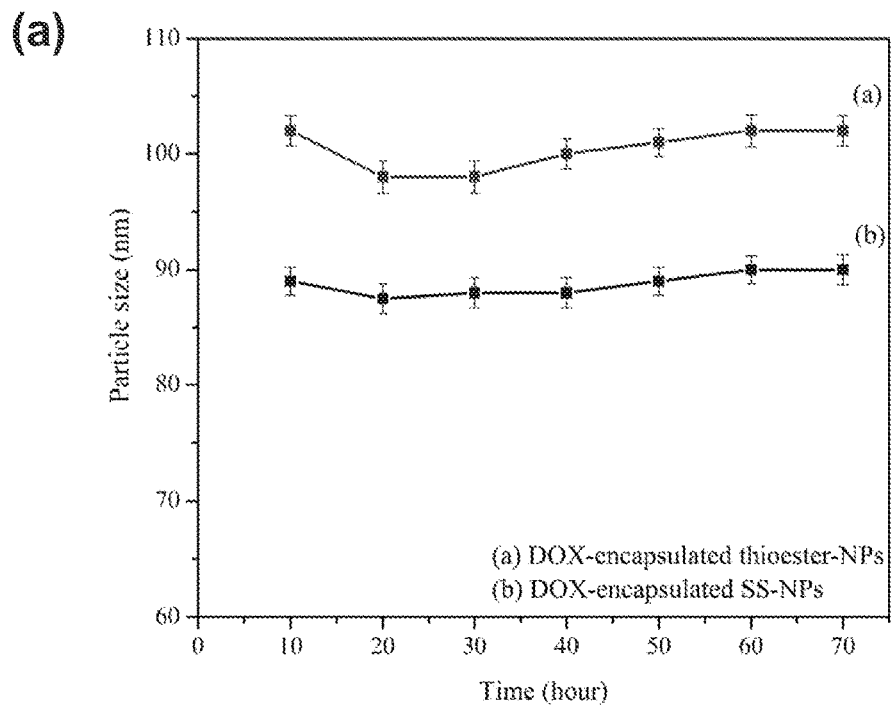
FIG. 4 (a) shows stability of DOX-encapsulated thioester-NPs and DOX-encapsulated SS-NPs in PBS/FBS (1:1) stored at 4° C., and FIG. 4 (b) shows release profiles of DOX-encapsulated thioester NPs and DOX-encapsulated SS-NPs with and without DTT in PBS buffer (pH 7.4, 10 mM) at 37° C.
Figure 4:
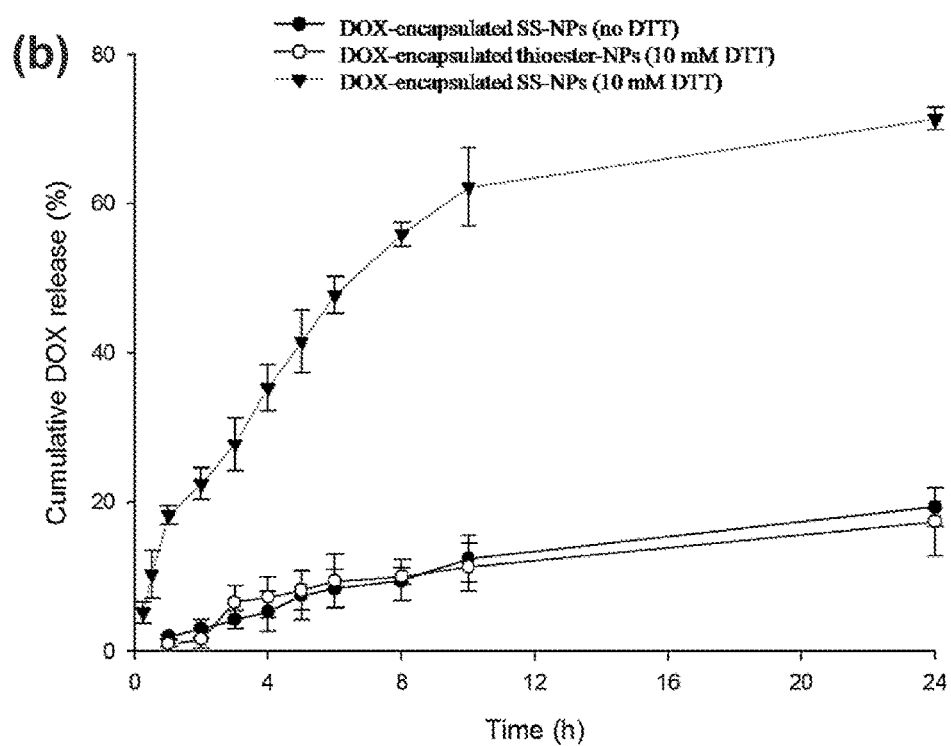

The DOX-encapsulated SS-NPs released DOX rapidly in the presence of 10 mM DTT, a reductive environment analogous to that of the intracellular compartment, showing 50% DOX release in 5 h and about 70% drug releases within 24 h. In contrast, minimal drug release (~10%) was observed after 24 h for the non-reducible PC5MA-PEO-thioester NPs under the same conditions as well as for PC5MA-SS-PEO NPs in the absence of DTT (FIG. 4b).

Example 6: Intracellular Uptake and Release Behavior of DOX-Encapsulated NPs is A549 and NIH-3T3 Cells A549 (cancer cells) and NIH3T3 (normal cells) cells were seeded at a density of $1.0 \times 10^5$ cells/well in an 8-well chamber of a Lab-Tek II chamber slide and preincubated for 24 h at 37° C. and 5% $CO_2$. Serum-free DMEM containing free DOX and DOX-NPs at equivalent doses (10 μg/mL) was added to each well, followed by incubation for 30 min, 2 h and 4 h at 37° C. The cells were then rinsed with PBS, and fixed with 4% formaldehyde solution for 10 min. Cover glasses were then placed on glass slides. The cellular uptake and release behavior of DOX-encapsulated SS or thioester NPs were imaged by confocal laser scanning microscopy (CLSM) (Leica, England) at an excitation wavelength of 488 nm for DOX. Since DOX itself is fluorescent, it was used directly to investigate cellular uptake without additional fluorescent labeling in of the nanoparticles.

Figure 5:
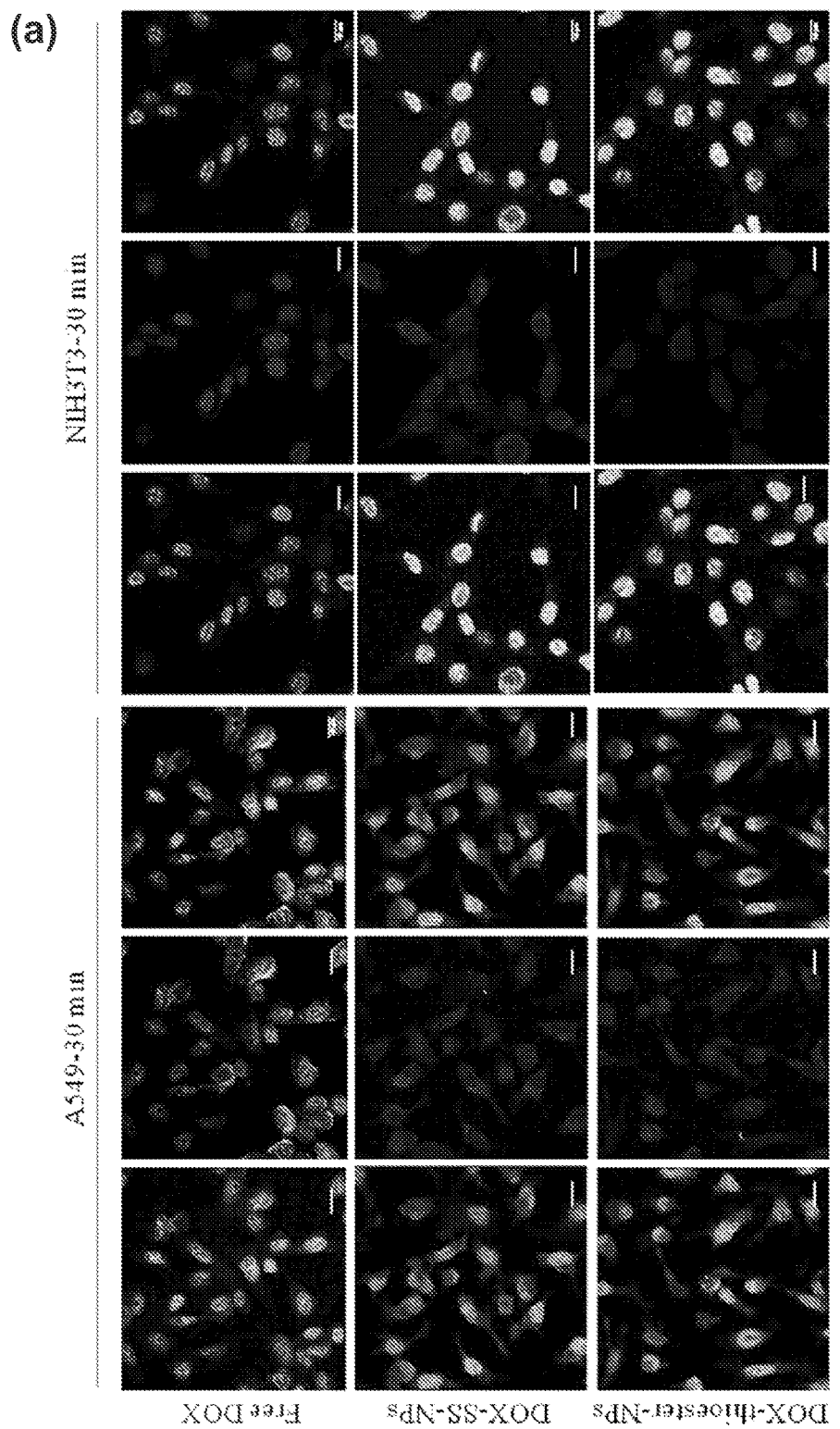
FIG. 5 shows confocal laser scanning microscopy (CLSM) images of A549 and fibroblast (NIH3T3) cells incubated with free DOX, DOX-encapsulated thioester-NPs, and DOX-encapsulated SS-NPs for 30 min (a), 2 h (b) and 4 h (c) at 10 μg/mL DOX equivalence. Scale bars are 10 μm. Blue-nuclei stained with DAPI; red-DOX.
Figure 5:
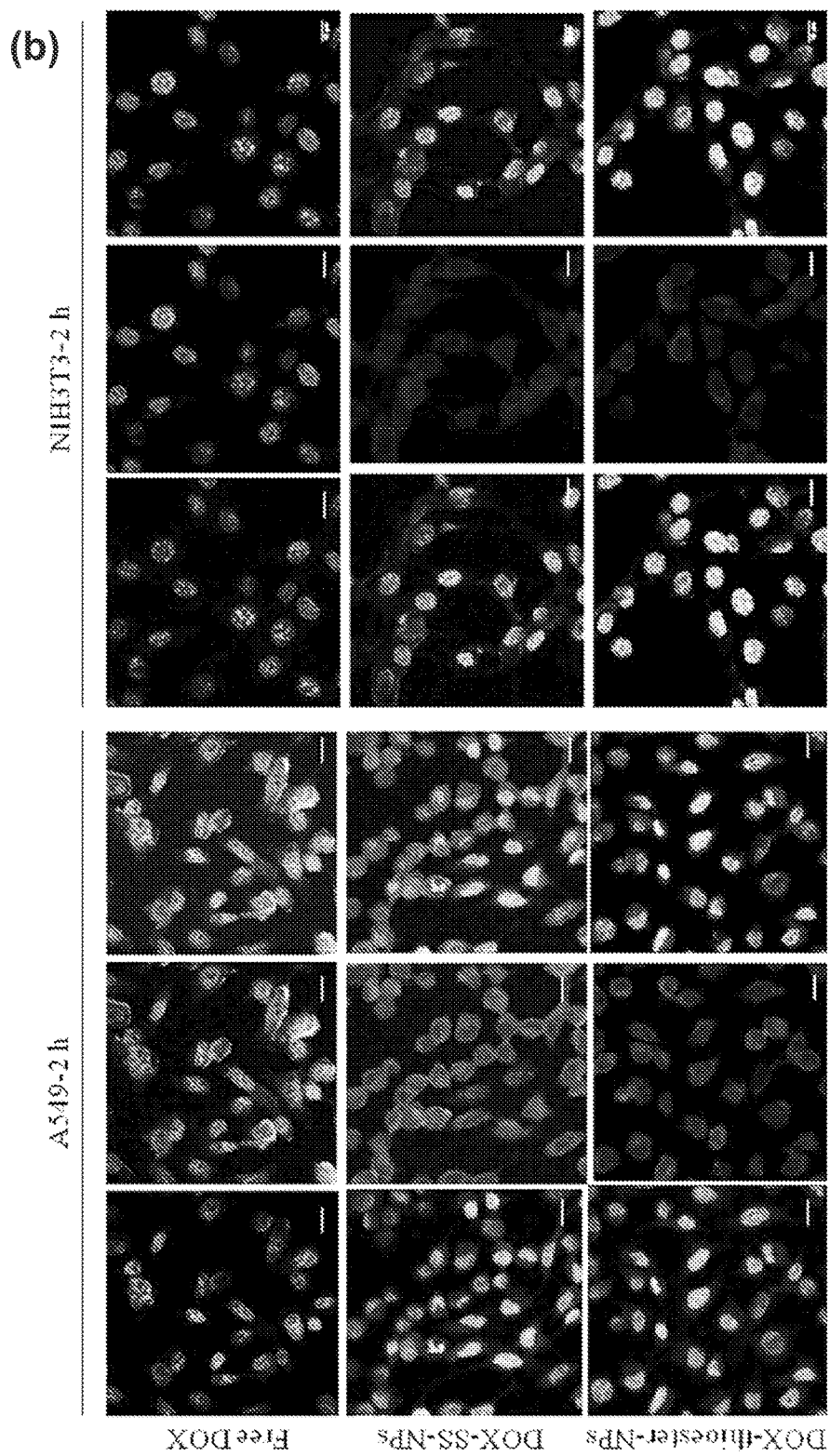
Figure 5:
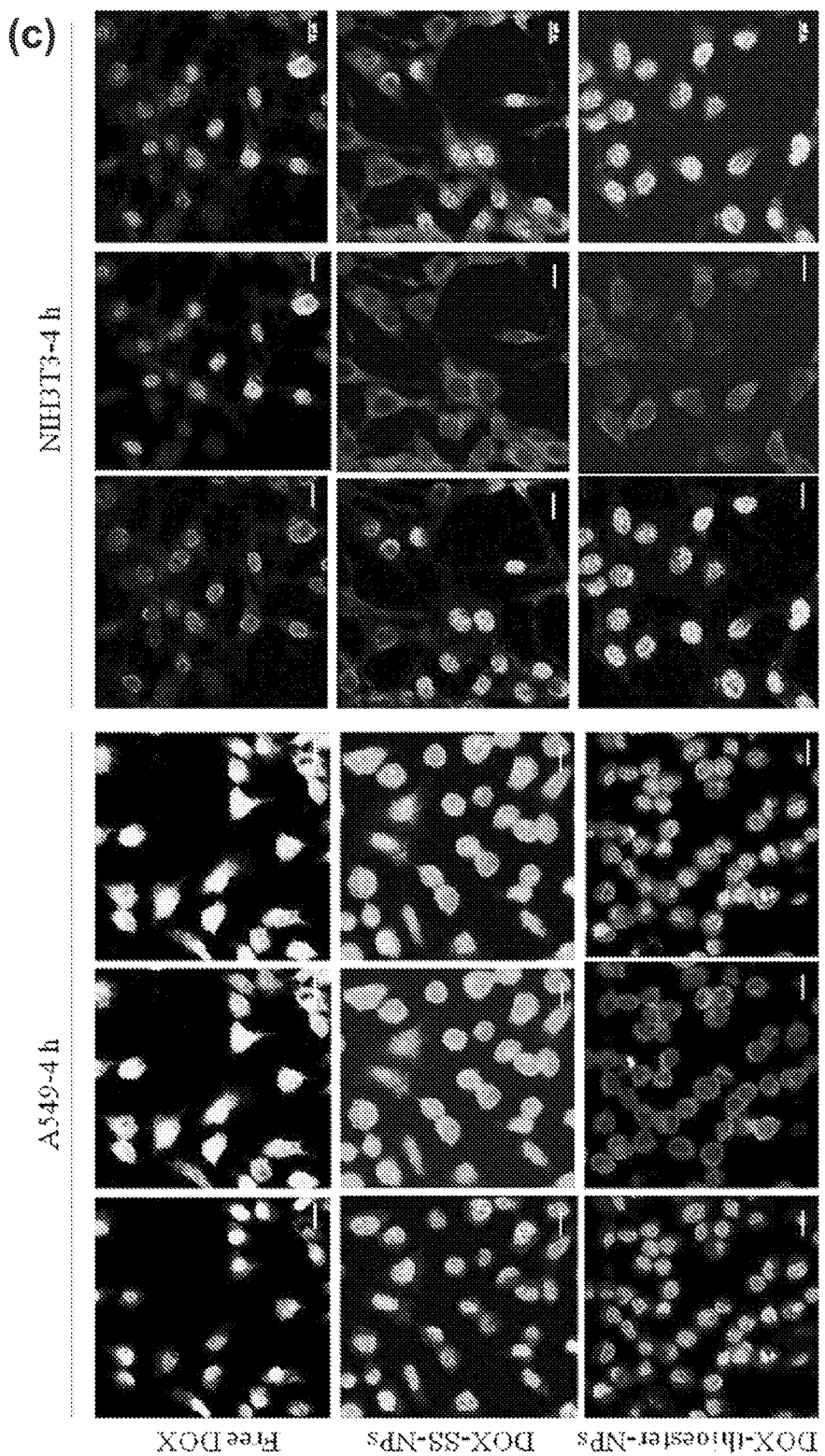

As shown in FIG. 5, when incubating A549 cells with DOX-encapsulated thioester-NPs and DOX-encapsulated SS-NPs for 30 min, the red fluorescent signal was observed mainly in the cytoplasm while free DOX entered the cellular nuclei. By increasing the incubation time to 2 h and 4 h, free DOX and DOX-encapsulated SS-NPs showed a strong red signal in the cellular nuclei (FIG. 5a), whereas DOX-encapsulated thioester-NPs still remained in the cytoplasm (FIG. 5b-c). In contrast, the intracellular drug release from non-reducible DOX-encapsulated thioester-NPs was negligible under the same conditions. As a negative control, NIH3T3 cells were utilized to compare cellular uptake of DOX-encapsulated thioester-NPs and DOX-encapsulated SS-NPs. When the cells were incubated with free DOX, red signal was observed in the cellular nuclei at all the time points from 30 min to 4 h. When the cells were exposed to DOX-encapsulated thioester-NPs and DOX-encapsulated SS-NPs, the red fluorescent signal was visualized mainly in the cytoplasm up to 4 h (FIG. 5 a-c). The results indicated that DOX release from the redox-sensitive nanoparticles was negligible in normal cells such as NIH3T3 during 4 h of incubation.

Example 7: Cytotoxicity of DOX-Encapsulated NPs in A549 and NIH3T3 Cells

A549 and NIH3T3 cells (7500 cells/well) were seeded on 96-well plates and cultured in 200 μL of DMEM supplemented with 10% FBS, 1% antibiotics, and 1% L-glutamine for 24 h at 37° C. and 5% $CO_2$. After incubation, various concentrations of DOX-encapsulated SS or thioester NPs and free DOX (1-50 μg/mL of DOX equivalents) dissolved in DMEM without supplements were added. After 24 h of incubation, cytotoxicity was determined using 3-[4,5-dimethylthiazol-2-yl]-3,5-diphenyltetrazolium bromide dye (MTT dye, final concentration of 0.5 mg/mL) uptake at 540 nm on a microplate reader (Tecan group Ltd., Mannedorf, Switzerland).

Figure 6:
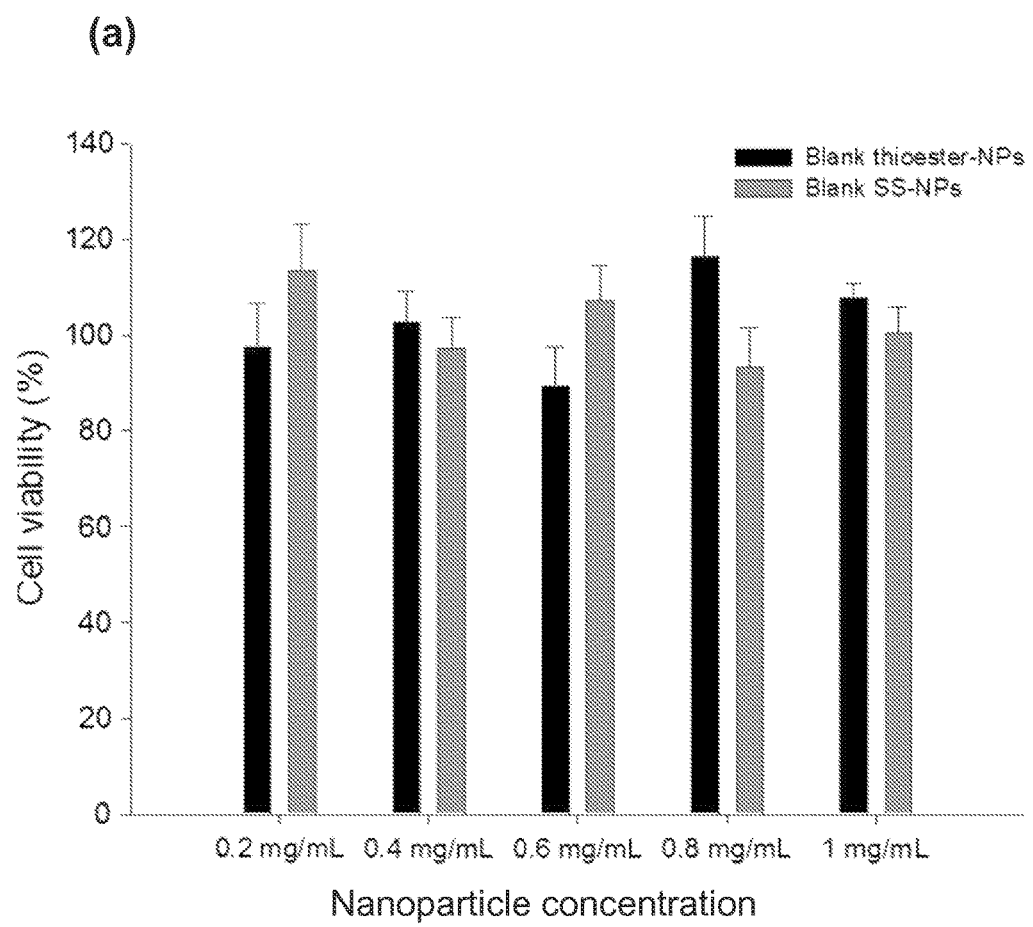
FIG. 6 shows viability of A549 cells incubated with blank thioester-NPs and blank SS-NPs for 24 h (a), with free DOX, DOX-encapsulated thioester-NPs, and DOX-encapsulated SS-NPs (b), and cell viability of NIH3T3 cells incubated with free DOX, DOX-encapsulated thioester-NPs, and DOX-encapsulated SS-NPs (c) at different concentrations of DOX for 24 h.
Figure 6:
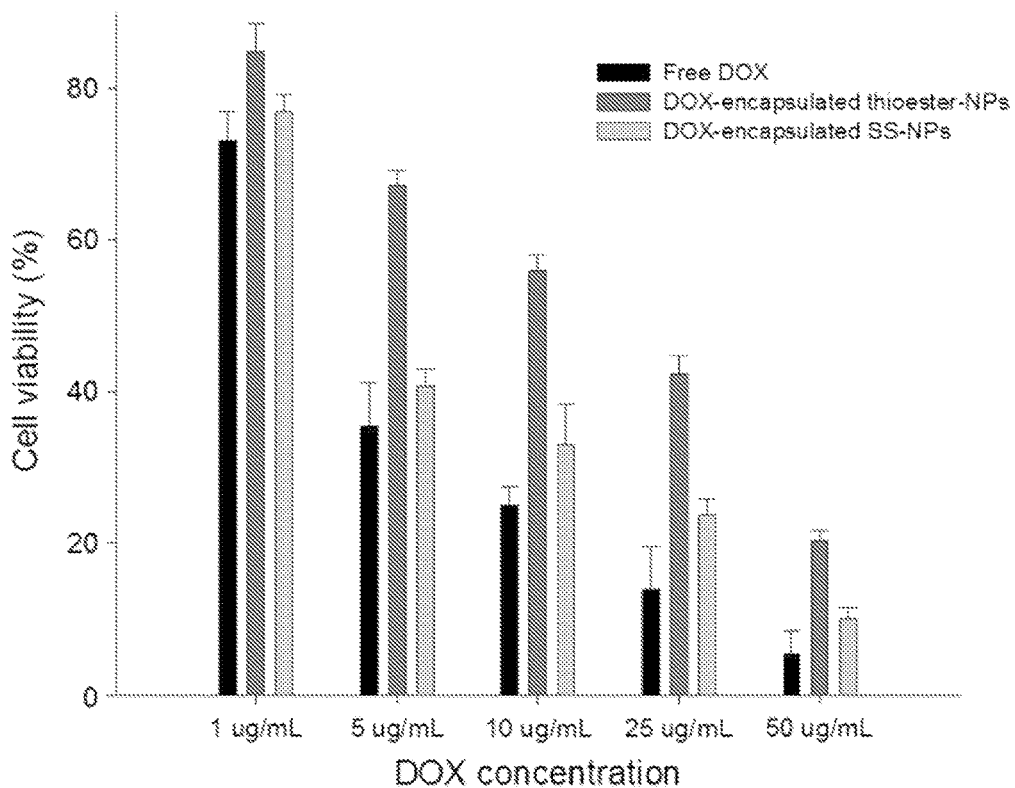
Figure 6:
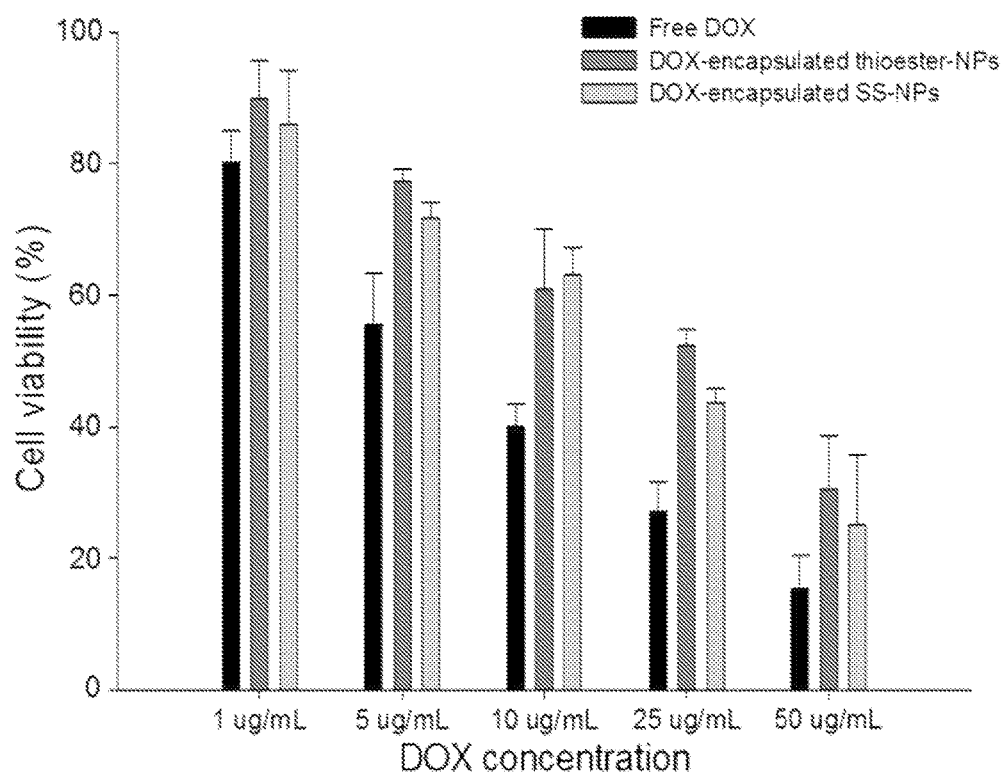

In vitro cytotoxicity of DOX-encapsulated thioester-NPs and DOX-encapsulated SS-NPs was compared with that of free DOX in A549 and NIH3T3 cells using the MTT assay. FIG. 6 show the viability of A549 and NIH3T3 cells treated with blank nanoparticles, free DOX, DOX-encapsulated thioester-NPs and DOX-encapsulated SS-NPs at different equivalent DOX concentrations. Blank thioester-NPs and SS-NPs showed negligible toxicity to A549 cells even at a concentration of 1 mg/mL, with a cell viability >90% after 24 h treatment, indicating good compatibility of the nanoparticles to A549 cells (FIG. 6a). Free DOX and DOX-encapsulated nanoparticles decreased the cell viability by 5-82% after 24 h of incubation in a dose-dependent manner (1-50 µg/mL DOX) (FIG. 6b). By increasing DOX concentration from 1 µg/mL to 50 µg/mL, free DOX and DOX-encapsulated SS-NPs drastically decreased the cell viability while the DOX-encapsulated thioester-NPs gradually decreased the cell viability. At all DOX concentrations, the cytotoxicity of free DOX and DOX-encapsulated SS-NPs was significantly higher than that of DOX-encapsulated thioester-NPs. In NIH3T3 cells, the toxicity of DOX-encapsulated thioester-NPs was comparable to that of DOX-encapsulated SS-NPs at all tested DOX concentrations (FIG. 6c).

Example 6: Intracellular Uptake and Release Behavior of DOX-Encapsulated NPs in HeLa Cells To observe the cellular uptake, HeLa cells (cancer cells) were seeded at a density of $1.0 \times 10^5$ cells/well in an 8-well chamber of a Lab-Tek II chamber slide and preincubated for 24 h at 37° C. and 5% $CO_2$. Serum-free DMEM containing free DOX and DOX-NPs at equivalent doses (25 µg/mL) was added to each well, followed by incubation for 2 h at 37° C. The cells were then rinsed with PBS, stained with 10 µM Draq5 and fixed with 4% formaldehyde solution for 10 min. Cover glasses were then placed on glass slides. The cellular uptake of free DOX and DOX-NPs was imaged by CLSM at an excitation wavelength of 488 nm for DOX. To quantify cellular uptake, HeLa cells ($5 \times 10^5$ cells/well) in 0.5 mL were grown on a 24-well plate at 37° C. in a humidified atmosphere of 5% $CO_2$ for 24 h. Serum-free DMEM containing free DOX and DOX-NPs at equivalent doses (25 µg/mL) was added to the cells which were subsequently incubated for 2 h. The cells were then washed three times with PBS, harvested by trypsinization and transferred into Fluorescence Activated Cell Sorter (FACS) tubes. All samples were analyzed by flow cytometry (FACSCalibur, BD Biosciences, San Jose, Calif.) to determine cellular internalization. Fluorescence measurements of intracellular DOX were performed in the FL2 channel.

Figure 7:
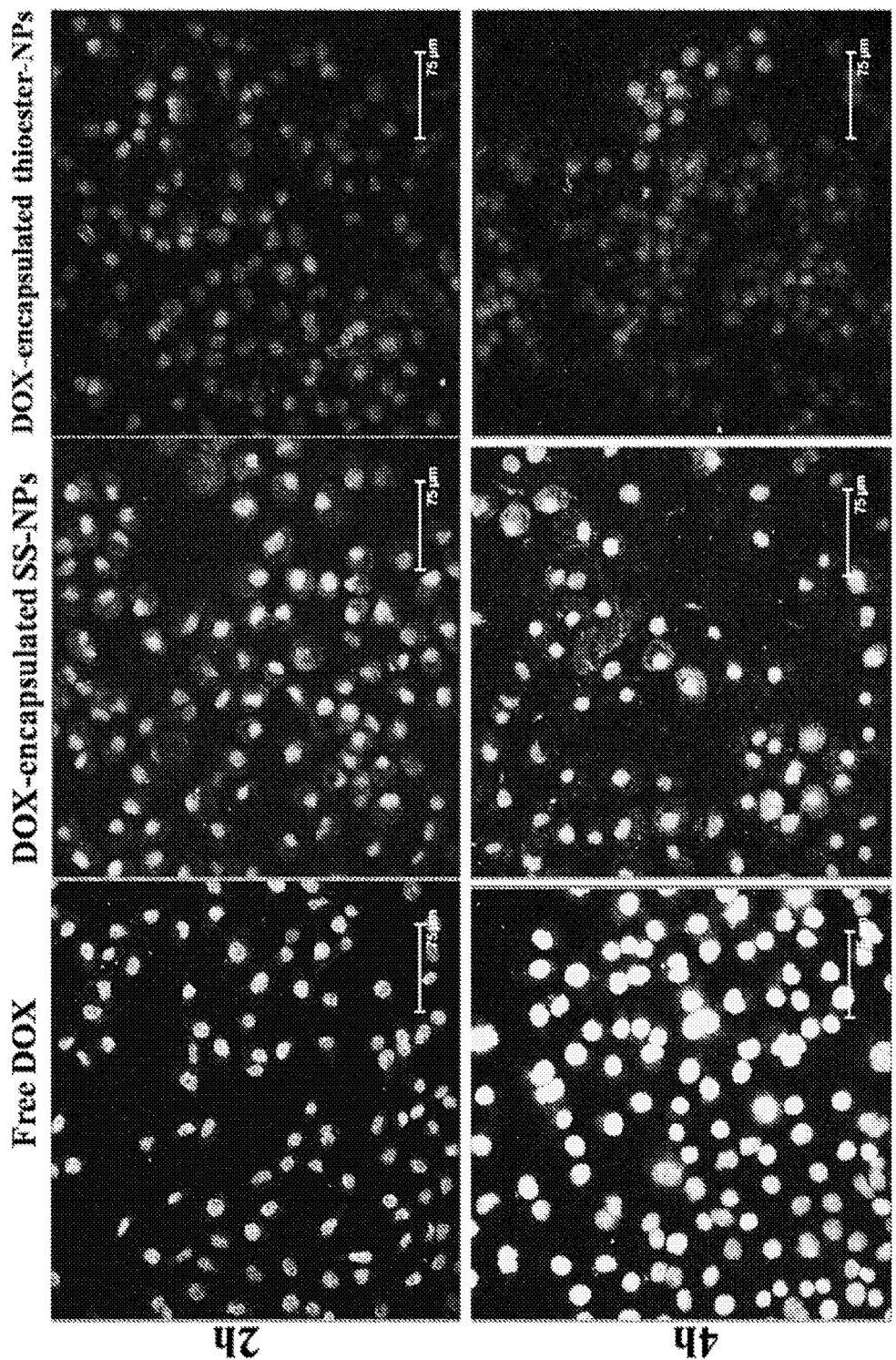
FIG. 7 shows CLSM images of HeLa cells incubated with free DOX, DOX-encapsulated thioester nanoparticles, and DOX-encapsulated SS nanoparticles for 2 h and 4 h at 10 μg/mL DOX equivalence.

As shown in FIG. 7, after 2 h of incubation, the red fluorescent signal was observed in free DOX and DOX-encapsulated SS-NPs-treated cells, whereas weak red fluorescent signal was observed in DOX-encapsulated thioester-NPs-treated cells. Increasing the incubation time to 4 h, free DOX and DOX-encapsulated SS-NPs-treated cells showed significant increases in the red signal, whereas DOX-encapsulated thioester-NPs-treated cells presented negligible red signals. In addition, treatment of Hela cells with free DOX, DOX-encapsulated thioester-NPs and DOX-encapsulated SS-NPs for 4 h produced cell shrinkage and blebbing, indicating the cytotoxicity effect of DOX in the nanoparticles. It is well known that nanoparticles with ideal size are accumulated within the tumor microenvironment by EPR effect. The accumulation within tumor tissues may not always correlate with therapeutic outcome since cellular internalization is required for anticancer drugs to exert their biological function inside tumor cells. The efficient cellular uptake and drug release of DOX-encapsulated SS-NPs indicate a greater drug efficacy and improves the therapeutic effect of DOX against cancers.

Example 9: Cytotoxicity of DOX-Encapsulated NPs in HeLa Cells

HeLa cells (7500 cells/well) were seeded on 96-well plates and cultured in 200 µL of DMEM supplemented with 10% FBS, 1% antibiotics, and 1% L-glutamine for 24 h at 37° C. and 5% $CO_2$. After incubation, various concentrations of the blank nanoparticles (0.2-1 mg/mL), DOX-NPs, and free DOX (1-50 µg/mL of DOX equivalents) dissolved in DMEM without supplements were added. After 24 h of incubation with free DOX and DOX-NPs, and 48 h with blank nanoparticles, cytotoxicity was determined using 3-[4, 5-dimethylthiazol-2-yl]-3,5-diphenyltetrazolium bromide dye (MTT dye, final concentration of 0.5 mg/mL) uptake at 540 nm on a microplate reader (Tecan group Ltd., Männedorf, Switzerland).

Figure 8:
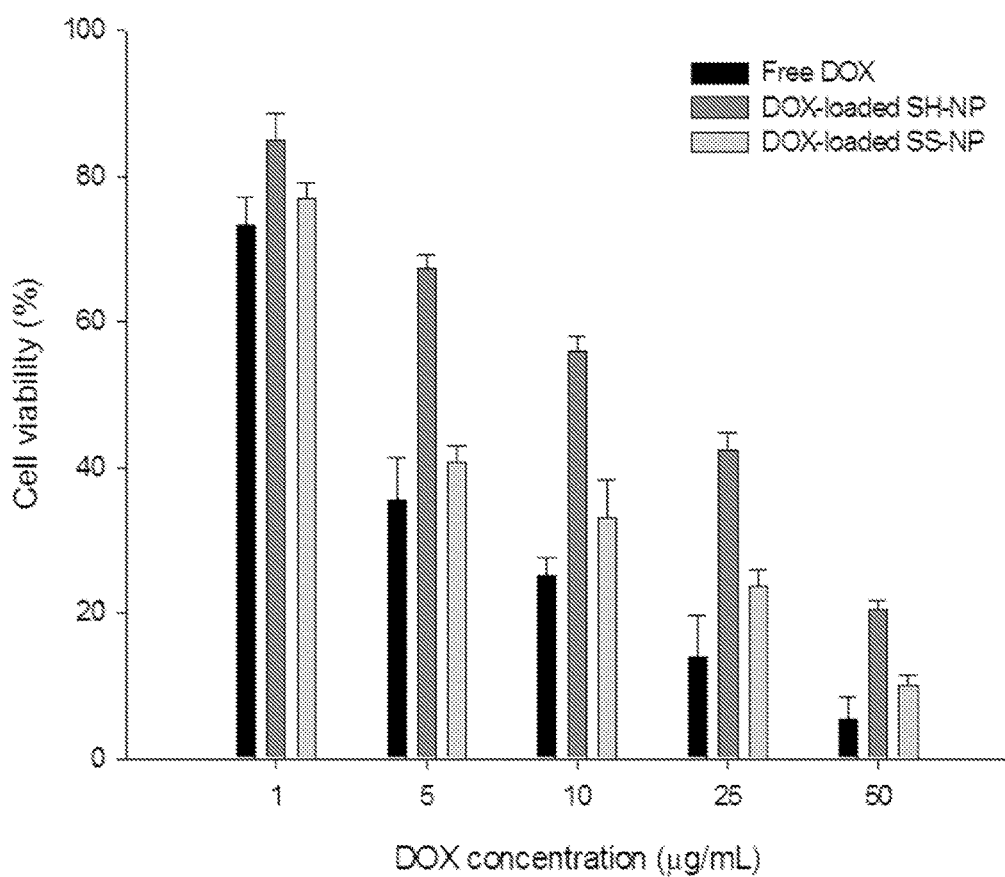
FIG. 8 shows viability of Hela cells incubated with free DOX, DOX-encapsulated thioester-NPs, and DOX-encapsulated SS-NPs at different concentrations of DOX for 4 h.

FIG. 8 shows the viability of Hela cells treated with free DOX, DOX-encapsulated thioester-NPs and DOX-encapsulated SS-NPs at different nanoparticles and equivalent DOX concentrations. Free DOX, DOX-encapsulated thioester-NPs and DOX-encapsulated SS-NPs dose-dependently (1-50 µg/mL DOX) decreased the cell viability by 80-90% after 4 h of incubation. Increasing DOX concentration from 1 µg/mL to 5 µg/mL and up to 50 µg/mL, free DOX significantly decreased the cell viability while the DOX-encapsulated NPs gradually decreased the cell viability. At all DOX concentrations, free DOX showed significantly higher cytotoxicity than DOX-encapsulated NPs, possibly due to the difference in the uptake pathway of free DOX and DOX-encapsulated NPs, and the sustained-release property of DOX-encapsulated NPs. At similar DOX level, the cytotoxicity of DOX-encapsulated SS-NPs was significantly lower than that of DOX-encapsulated thioester-NPs, indicating that DOX-encapsulated SS-NPs taken up by cells were release DOX in the free form.

Example 8: In Vivo Imaging of PC5MA-SS-PEONPs

The biodistribution of PC5MA-SS-PEO NPs was assessed by in-vivo near-infrared (NIR) imaging. A NIR fluorophore, DiR, was loaded into the nanoparticles by a dialysis method. Briefly, the PC5MA-SS-PEO (10 mg) and DiR (0.6 mg) were dissolved in DMF (3 mL). The resulting solution was dialyzed against distilled water for 48 h, and then filtered through a 0.45 µm membrane before lyophilization. The loading content of DiR was determined spectrophotometrically at a wavelength of 750 nm. The tumor models were established by subcutaneous injection of A549 cells ($2 \times 10^6$ cells in 100 µL of PBS) into the flank of male SCID mice. When the tumor reached an acceptable size, the mice were treated with the DIR-loaded NPs (5 µg/kg of equivalent DiR) via tail-vein injection. Whole body images were obtained at 1 h, 3 h, 6 h, 24 h, 48 h and 72 h after injection using an IVIS imaging system (PerkinElmer, Hopkinton, Mass., USA). Images of various organs, including heart, kidney, liver, spleen, lung, antitumor, were also obtained after sacrifice of the mice at 72 h post-injection.

Figure 9:
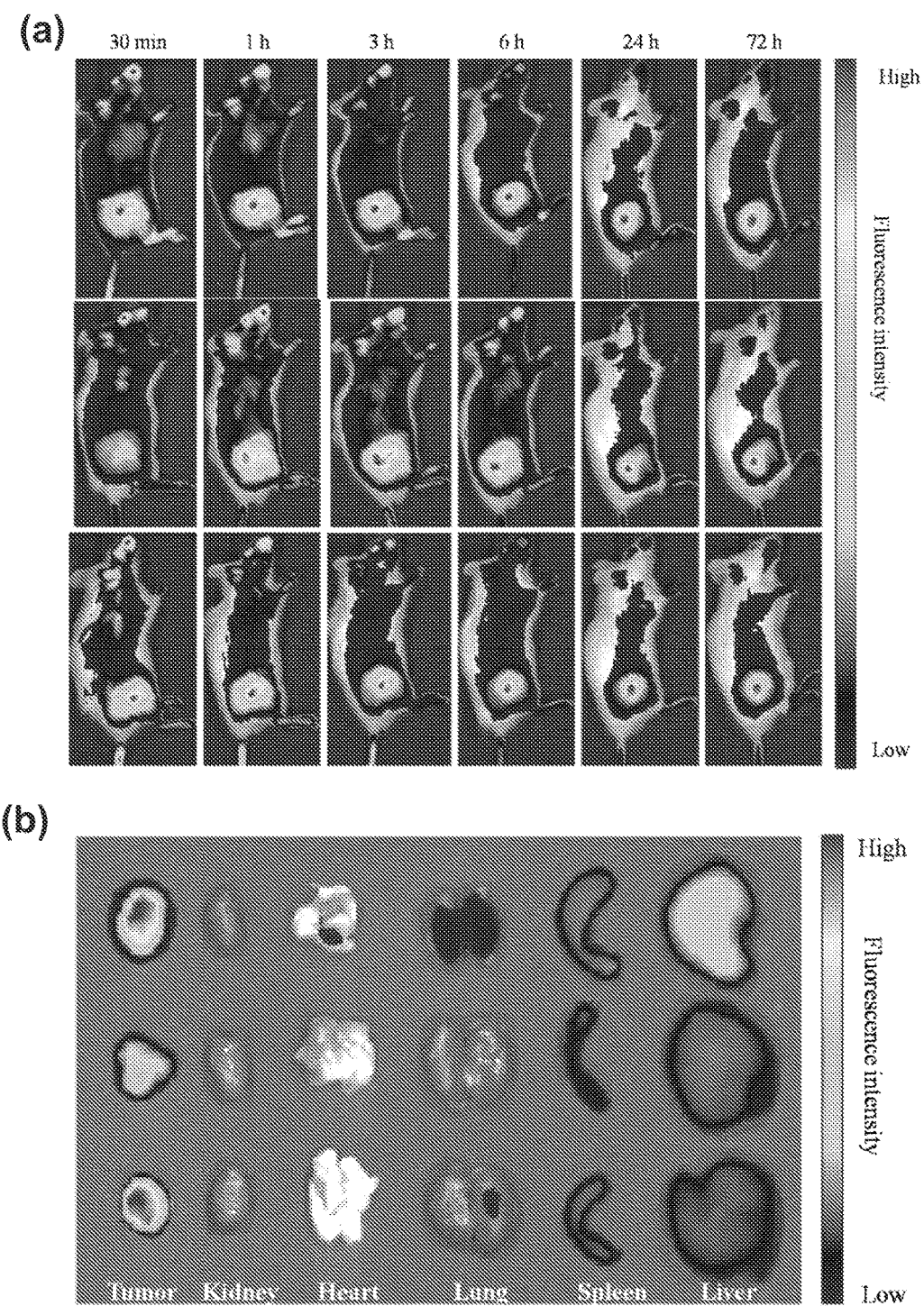
FIG. 9 shows (a) in vivo fluorescence images of DiR-encapsulated SS-NPs in tumor-bearing SCID mice at 1 h, 3 h, 6 h, 24 h, 48 h, and 72 h-post intravenous injection; and (b) ex vivo images of tumors and organs at 72 h-post injection.

A hydrophobic NIRF dye, DiR was used as a model drug for encapsulation into PC5MA-SS-PEO NPs (5% wiw). DiR release from SS-NPs was investigated in simulated physiological condition and the result showed less than 7% of DiR release during 24 h without any burst release, indicating the stability of DiR in the nanoparticles. This dye emits strong NIR fluorescence that is minimally absorbed by water or hemoglobin. This enables less interference from background fluorescence during non-invasive animal imaging. The DiR-loaded PC5MA-SS-PEO NPs were administrated to the A549 tumor-bearing SCID mice via tail-vein injection. At 1 h and 3 h post-injection, a fluorescence signal could be detected throughout the entire animal. The fluorescent signal in the liver was relatively weaker than the tumor signal (FIG. 9a). Moreover, the contrast of the DiR signal in the tumor compared to the surrounding tissues of the animal was already apparent 6 h post-injection of the PC5MA-SS-PEO NPs in two mice, and even at 1 h post-injection in one mouse. At 24 h post-injection, a strong red signal was observed in tumor tissues and only a low signal was observed in the liver. This strong fluorescence signal in the tumors was maintained up to 72 h post-injection. After this time the mice were sacrificed and the major organs were isolated to analyze the tissue distribution of the DiR-loaded nanoparticles. As shown in FIG. 9b, the highest NIRF intensity was observed in tumor tissues, while the signal intensities were lower for other tissues such as liver, without any detectable fluorescence signal in the heart.

Results

The as-synthesized block copolymers readily self-assembled in aqueous solution to form nanoparticles due to the hydrophobic interaction between the cholesterol moieties. The CMC values were in the typical range of PEG-based block copolymers, suggesting that the PC5MA-SS-PEO copolymers may circulate as self-assembled nanoparticles in vivo for an extended period of time. These nanoparticles have a core/shell structure bearing a hydrophobic cholesterol inner core that could encapsulate hydrophobic drugs. DOX-encapsulated PC5MA-SS-PEO and PC5MA-PEO-thioester NPs had size less than 100 nm and negatively charged surface. It has been reported that the ideal size for self-assembled nanoparticles to evade renal clearance and liver capture is >10 nm and <100 nm, respectively. Therefore, the reducible NPs have sizes and surface charges that are suitable for tumor targeting via the EPR effect.

In a reductive environment of DTT, particle size of DOX-encapsulated PC5MA-SS-PEO NPs significantly increased, indicating the nanoparticles were unstable. Furthermore, no particle size was detectable after 4 h of incubation, indicating a complete dissociation of the nanoparticles. This was due to the presence of disulfide bonds, which made NPs breakable in the reductive environment. These results suggest that PC5MA-SS-PEO NPs remains stable during systematic blood circulation but rapidly dissociate and release DOX in a reductive intracellular environment due to the cleavage of disulfide linker between PC5MA and PEO blocks. This result was consistent with the previous observation that PC5MA-SS-PEO NPs were destabilized in response to 10 mM DTT. It should be further noted that the DOX-encapsulated SS-NPs released DOX in a sustained release pattern without an initial burst release in PBS in the absence of DTT. The release behavior of the PC5MA-SS-PEO NPs is useful for delivery of anticancer drugs, in which limited amounts of the drug are released in the blood stream until the nanoparticles reach the tumor tissues where the drug release is triggered inside cancer cells due to the dissociation of the nanoparticles in the presence of high intracellular GSH concentration.

The results of in vitro experiments indicated the fast dissociation of DOX-encapsulated SS-NPs in the intracellular reductive condition which triggered the release of DOX molecules resulting in the fast drug influx into the nuclei as evident by the cellular uptake study in cancer cells versus normal cells. The triggered DOX release from DOX-encapsulated SS-NPs resulted in significant higher cytotoxicity effect compared to non-reducible NP. It is well known that nanoparticles with ideal sizes accumulate within the tumor microenvironment by the EPR effect. However, the accumulation within tumor tissues may not always correlate with therapeutic outcome since cellular internalization is required for anticancer drugs to exert their biological function inside tumor cells. The results suggest that the efficient cellular uptake and drug release of DOX-encapsulated SS-NPs improves the therapeutic effect of DOX against cancers. In addition, the cytotoxicity results were further confirmed that DOX-encapsulated SS-NPs released DOX in the free form inside the cancer cells and induced its therapeutic effect. The results suggest that the PC5MA-SS-PEO NPs are effective for cancer-cell specific delivery of anticancer drugs.

To assess biodistribution of the PC5MA-SS-PEO NPs, in vivo fluorescence images of the PC5MA-SS-PEO NPs in tumor-bearing SCID mice were obtained using non-invasive near-infrared fluorescence (NIRF) imaging. The weak of fluorescent signal in the liver at 1 h and 3 h injection was consistent with previously reported cholesterol-containing nanoparticles (Tran et al. "Long circulating self-assembled nanoparticles from cholesterol-containing brush-like block copolymers for improved drug delivery to tumors." *Biomacromolecules*. 2014; 15:4363-75). The intense whole-body fluorescence was continuously observed at 6 h post-injection, indicating the prolong circulation time of the DiR-loaded PC5MA-SS-PEO NPs. The previous in vivo imaging study showed that free hydrophobic DiR accumulated in liver from 1 h to 24 h with negligible tumor accumulation (Tran et al. 2014). The results demonstrated the effective accumulation of the PC5MA-SS-PEO NPs in tumor tissue. This appreciable tumor targeting ability of PC5MA-SS-PEO NPs may have resulted from the prolonged circulation time achieved by the stability of the nanoparticles and the EPR effect in tumor tissue due to their small size, which favored tumor accumulation with reduced capture by the liver. Once accumulated in the tumor tissues, therapeutic effect of DOX may be enhanced by the triggering effect of the reducible NPs to release DOX from NPs and rapidly diffuse into tumor cell nuclei.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A copolymer comprising:
a first block, which is of formula:

and a second block, which is of formula:

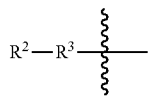

wherein m is an integer about 3 to about 500;

A is independently selected from the group consisting of polyacrylate, polymethacrylate, polynorbonene, polycyclopentene, polycyclooctene, polysiloxane, polyester, and polypeptide, or combinations thereof;

$R^1$ is a steroid moiety optionally comprising a linker $R^{11}$;

$R^2$ is polyalkylene oxide, polyester, or polypeptide moiety; and $R^3$ is a disulfide linker moiety.

2. The copolymer of claim 1, wherein the steroid moiety comprises cholesterol, cholic acid, deoxycholic acid, taurocholic acid, lanosterol, estradiol, testosterone, bile acid, dexamethasone, secosteroid, phytosterol, or combinations thereof.

3. The copolymer of claim 1, wherein $R^{11}$ is

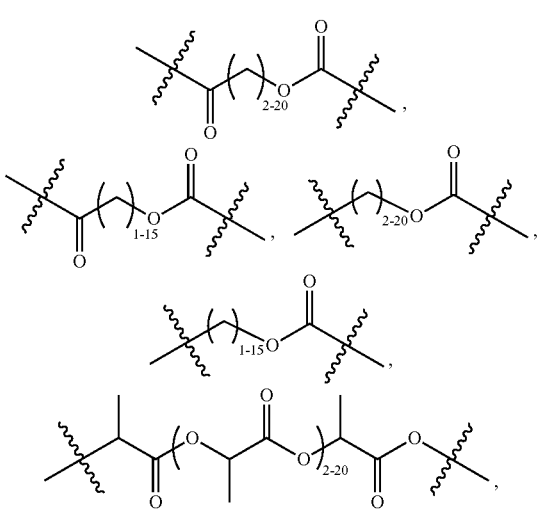

a polylactone, or an oligomer of siloxane.

4. The copolymer of claim 1, wherein A is independently polyacrylate, polymethacrylate, polyester, or a combination thereof.

5. The copolymer of claim 1, wherein the first block is of formula:

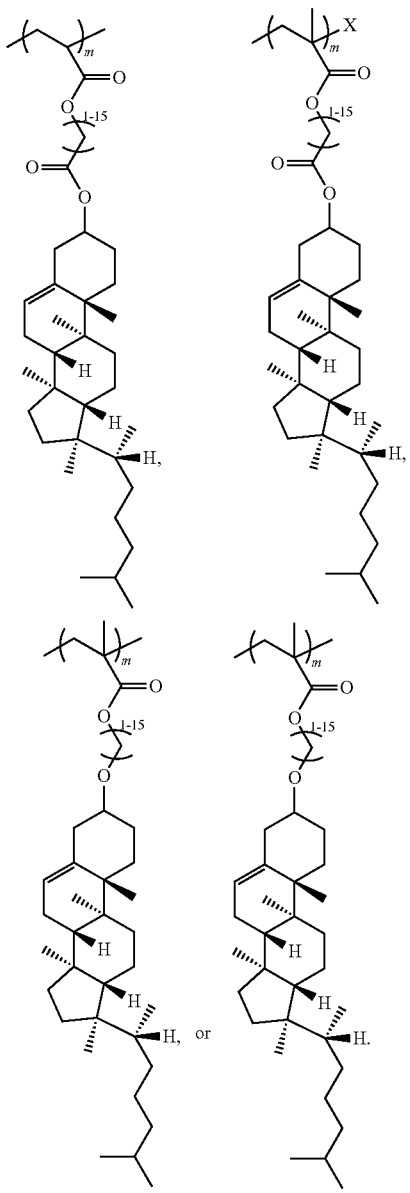

6. The copolymer of claim 1, wherein $R^2$ is a polyalkylene oxide moiety.

7. The copolymer of claim 6, wherein the polyalkylene oxide moiety comprises polyethylene oxide, polyethylene oxide thiolate, polypropylene oxide, or polypropylene oxide thiolate.

8. The copolymer of claim 1, wherein $R^3$ is of formula:

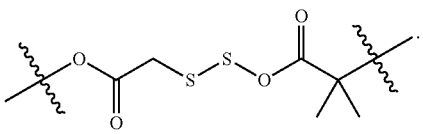 [SMILES: *OC(=O)CSSOC(=O)C(*)(C)C]

9. The copolymer of claim 1, wherein the copolymer further comprises a chain terminus X:

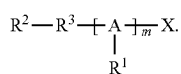

10. The copolymer of claim 9, wherein X is a trithiocarbonate, dithiocarbamate, or dithioester.

11. The copolymer of claim 9, wherein X is —SC(S)S—C$_{12}$H$_{25}$.

12. The copolymer of claim 9, comprising the structure:

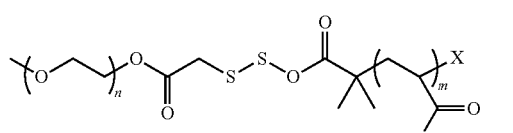

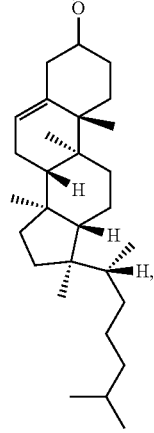

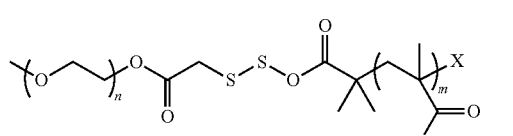

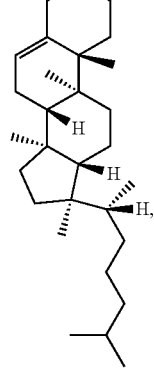

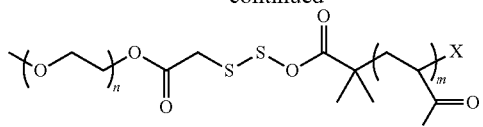

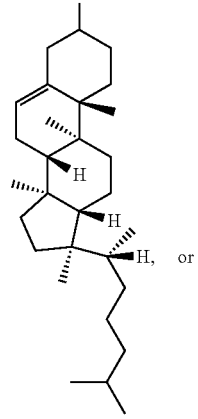

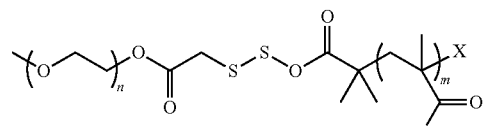

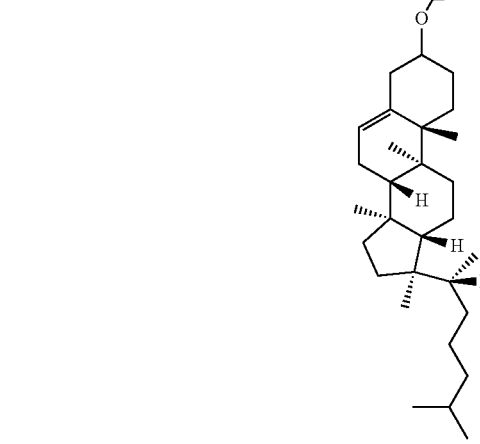

wherein
m is an integer between about 5 and about 200; and
n is an integer between about 5 and about 100.

13. The copolymer of claim 1, wherein m is between about 10 and about 100.

14. The copolymer of claim 1, wherein the molecular weight of the copolymer is about 5,000 Da to about 200,000 Da.

15. The copolymer according to claim 1, wherein the copolymer is in a core/shell nanoparticle form.

16. A nanoparticle comprising the copolymer of claim 15 and a pharmaceutically active molecule.

17. The nanoparticle of claim 16, wherein the molecule is doxorubicin, daunorubicin, vincristin, paclitaxel, docetaxel, cisplatin, camptothecin, irinotecan, 5-fluorouracil, methotrexate, or dexamethasone.

18. The nanoparticle of claim 15, further comprising one or more metal nanoparticles or quantum dots (e.g., near infrared (NIR) quantum dot).

19. A method of delivering a pharmaceutically active molecule, or of treating a disease or disorder comprising administering to a subject in need thereof the nanoparticle according to claim 16.

20. A process for preparing the nanoparticle according to claim 15, comprising: (a) dissolving a copolymer in an organic solvent to obtain a copolymer solution; and (b) mixing the copolymer solution in an aqueous solution to form a nanoparticle; wherein the copolymer comprises:

a first block, which is of formula:

and a second block, which is of formula:

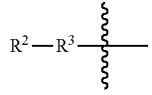

wherein m is an integer about 3 to about 500;

A is independently selected from the group consisting of polyacrylate, polymethacrylate, polynorbonene, polycyclopentene, polycyclooctene, polysiloxane, polyester, and polypeptide, or combinations thereof;

$R^1$ is a steroid moiety optionally comprising a linker $R^{11}$;

$R^2$ is polyalkylene oxide, polyester, or polypeptide moiety; and $R^3$ is a disulfide linker moiety.

* * * * *